(12) United States Patent
Johnson et al.

(10) Patent No.: US 10,402,539 B2
(45) Date of Patent: Sep. 3, 2019

(54) INTEGRATED SERVICES QUALIFICATION

(71) Applicant: Experian Health, Inc., Franklin, TN (US)

(72) Inventors: Daniel Erick Johnson, Wayzata, MN (US); Matthew Baltzer, Costa Mesa, CA (US); Heather Renee Grover, Trabuco Canyon, CA (US)

(73) Assignee: EXPERIAN HEALTH, INC., Franklin, TN (US)

( * ) Notice: Subject to any disclaimer, the term of this patent is extended or adjusted under 35 U.S.C. 154(b) by 828 days.

(21) Appl. No.: 15/083,508

(22) Filed: Mar. 29, 2016

(65) Prior Publication Data

US 2017/0235901 A1 Aug. 17, 2017

Related U.S. Application Data

(60) Provisional application No. 62/296,396, filed on Feb. 17, 2016.

(51) Int. Cl.
*G06F 19/00* (2018.01)
*G06Q 10/06* (2012.01)
*G16H 40/63* (2018.01)

(52) U.S. Cl.
CPC ........... *G06F 19/328* (2013.01); *G06Q 10/06* (2013.01); *G16H 40/63* (2018.01)

(58) Field of Classification Search
CPC ....... G06F 19/328; G16H 40/63; G06Q 10/06
See application file for complete search history.

(56) References Cited

U.S. PATENT DOCUMENTS

| | | | | |
|---|---|---|---|---|
| 2017/0147650 | A1* | 5/2017 | Hattori | G06F 16/24564 |
| 2017/0235901 | A1* | 8/2017 | Johnson | G06F 19/328 705/2 |
| 2017/0255759 | A1* | 9/2017 | McGrath | G06F 19/3456 |
| 2017/0277838 | A1* | 9/2017 | Derer | G06F 19/328 |
| 2017/0286495 | A1* | 10/2017 | Ott | G06F 16/2462 |

\* cited by examiner

*Primary Examiner* — Daniel D Chang
(74) *Attorney, Agent, or Firm* — Merchant & Gould

(57) ABSTRACT

Technical improvements to systems used to provide counseling regarding medical procedures and the payment therefor are discussed herein. A reduction in the amount of communications needed to provide financing for patients, when appropriate, is provided, which improves the efficiency of the systems used to process patients. Rather than transmitting sensitive data to multiple lenders to seek loan information, an internal risk assessment is developed, with the patient's consent, and used to provide pre-qualification during a cost-estimation phase of patient processing. Patients are thereby provided with greater flexibility in paying for healthcare services, which improves their access to healthcare and overall health, while providers are able to reduce regulatory and accounting burdens associated with patient delinquency.

10 Claims, 10 Drawing Sheets

Fig. 3

Upjohn, Emily
ACCT #: 00100200030004-1234
MRN: 987654321abc
Birth 01/01/1900
Service 01/01/2020

Status: Done ▼  Comments

PREV | NEXT

OVERVIEW / DEMOGRAPHICS / COVERAGE / PRE-CERTIFICATION / CHARITY / ESTIMATE / TRIAGE / COLLECTION / PT PORTAL

ESTIMATE

☑ Step 1: Pick Procedures

775015
Br. L Leg: Plaster Cast
Hackenbush, H.
$360.00   Qty 2 ❌

775016
Br. L Leg: Fiberglass Cast
Hackenbush, H.
$2,000.00   Qty 0 ❌

831594
Br. L Leg: Xray Series
Steinberg, L.
$80.00   Qty 1 ❌

☑ Step 2: Estimate Results   $800.00

Financing Available

Financing Options

1st Bank                          $800           ☐
Interest 0% for mo. 0-6, 5% for mo. 6+
2 year term                       Monthly Payment: $33.34/51.24

2nd Bank                          $800           ☑
Interest 2% monthly
2 year term                       Monthly Payment: $42.31

Apply          Defer

Authorization Required to Continue
Verify with patient that the information below is correct before continuing First Name: Emily         Address: 123 Oak St.
Last Name: Upjohn         City:    Anytown
SSN:       123-45-6789    State:   FL
DOB:       01/01/1900     ZIP:     33111

No Authorization    Verbal Authorization    Written Authorization

Patient Portal for:

Upjohn, Emily
ACCT #: 1234-56789-abcdef*123

Need assistance?
Email support  link
Chat with Support  link
Call Support  800-555-1234

Log Out

Preferences 280
410

Broken Leg — 01-Jan-2020

| | | |
|---|---|---|
| Standish San. | 2nd Bank<br>Interest 2% Monthly<br>2 year term | Good Standing  $701.98<br>Monthly Payment:  $42.31 |
| Ambulance Serv. | | Paid in Full |

420

Procedure History

| Action | Amt | Bal | Date |
|---|---|---|---|
| Treatment Begun | — | — | 01-Jan-2020 |
| Loan Approved | (800.00) | (800.00) | 01-Jan-2020 |
| Payment Rx'd | 42.31 | (757.69) | 01-Feb-2020 |
| Int @ 2% | (15.15) | (772.84) | 01-Feb-2020 |
| Payment Rx'd | 84.62 | (688.22) | 01-Mar-2020 |
| Int @ 2% | (13.76) | (701.98) | 01-Mar-2020 |

440

Service Loan

● Make Payment     Select Account ▶

○ Schedule Automatic Payment Plan    Set Amount

○ Pay Balance    Submit

430

Select other Procedures

| Cardiac Arrest<br>04-Nov-2016 | No Loan<br>Owe $15,738.89 | Apply for Loan<br>☐ 1st Bank<br>3% 5 year<br>☐ 2nd Bank<br>2% 4 year |
|---|---|---|
| Rotator Cuff<br>28-May-2017 | 1st Bank<br>Owe $854.00 | Service Loan |
| Carpal Tunnel<br>08-Mar-2017 | State Bank<br>Paid off on 01-Feb-2016 | |

INTEGRATED SERVICES QUALIFICATION

RELATED APPLICATIONS

This application claims priority from U.S. Provisional Patent Application No. 62/296,396 titled, "INTEGRATED SERVICES QUALIFICATION" and having a filing date of Feb. 17, 2016, which is incorporated herein by reference.

BACKGROUND

As the price of healthcare services increase, and as patients bear a larger portion of those costs, increasing strain is placed on the healthcare system. Patients delay or avoid medically necessary procedures for fear of going into debt, and healthcare providers are increasingly holding onto larger accounts receivable for longer periods of time, as patients and their insurance providers delay in making payments for procedures, or even default on payments for procedures. This places a strain on the healthcare system, in which healthcare providers must weigh the likelihood of receiving compensation for a given procedure against the benefit for the patient. Healthcare providers already use various computer systems to attempt to mitigate these risks, but these systems are limited in their speed and accuracy, which can lead the healthcare provider to limit which treatment options it makes available to patients due to perceived financial pressures, even when the patient is otherwise capable of paying for the unoffered procedures.

Currently, when patients seek healthcare services from healthcare providers, the computer systems of the healthcare providers (or their agents) perform various processes to provide healthcare services, and to bill for those services. These processes may include finding patients' healthcare coverage, verifying patient demographic data, determining a patient financial history (including checking payor compliance), estimating a charge for a procedure, and collecting payment for healthcare services, which are performed by separate systems. As will be appreciated, if the speed or accuracy at which individual systems perform these processes were to be improved, or the capabilities of these individual systems were to be expanded, the overall system itself and the quality of care available to patients would be improved.

SUMMARY

The present disclosure provides systems and methods for improving the functionality of service access workflow systems, such as the patient access workflow systems used by healthcare providers to process patients, the client access workflow systems used by attorneys to process clients, or the student access workflow systems used by educational institutions to process students. Although examples are presented primarily regarding the healthcare industry, these are presented as non-limiting examples, as service providers in other service industries may also make use of the present disclosure.

A reduction in the amount of communications and processing resources needed to offer assistance to patients, when appropriate, is provided, which improves the efficiency of patient access workflow systems. An internal risk assessment is developed, with the patient's consent, and used to provide pre-qualification during a cost-estimation phase of patient processing. In some aspects, rather than transmitting sensitive data to multiple lenders to seek loan information, an integrated system manages the presentation of loan data so that patients are provided multiple offers (or estimates of offers) and only the lender associated with a chosen offer is communicated with. The data used for the pre-qualification are stored as tokens, which are self-contained wrappers for the relevant data for a patient's pre-qualification that are transmittable between different systems and entities. If the patient, after being presented with pre-procedure loan offers, defers applying for one of the presented loans until after treatment, the tokens are used to later provide the patient with terms based on the initially provided terms without having to expend processor resources to recalculate the data after the procedure is performed. Patients are thereby provided with greater flexibility in paying for healthcare services, which improves their access to healthcare and overall health, while providers are able to reduce regulatory and accounting burdens associated with patient delinquency.

Aspects of systems and methods described herein may be practiced in hardware implementations, software implementations, and in combined hardware/software implementation. This summary is provided to introduce a selection of concepts; it is not intended to identify all features or limit the scope of the claimed subject matter.

BRIEF DESCRIPTION OF THE DRAWINGS

The accompanying drawings, which are incorporated in and constitute a part of this disclosure, illustrate various aspects and examples of the present invention. In the drawings:

FIG. 3 illustrates an example dashboard user interface as would be seen by a user during a pre-procedure price estimation phase;

FIG. 4 illustrates an example portal user interface as would be seen by a patient post-procedure;

DETAILED DESCRIPTION

Figure 1:
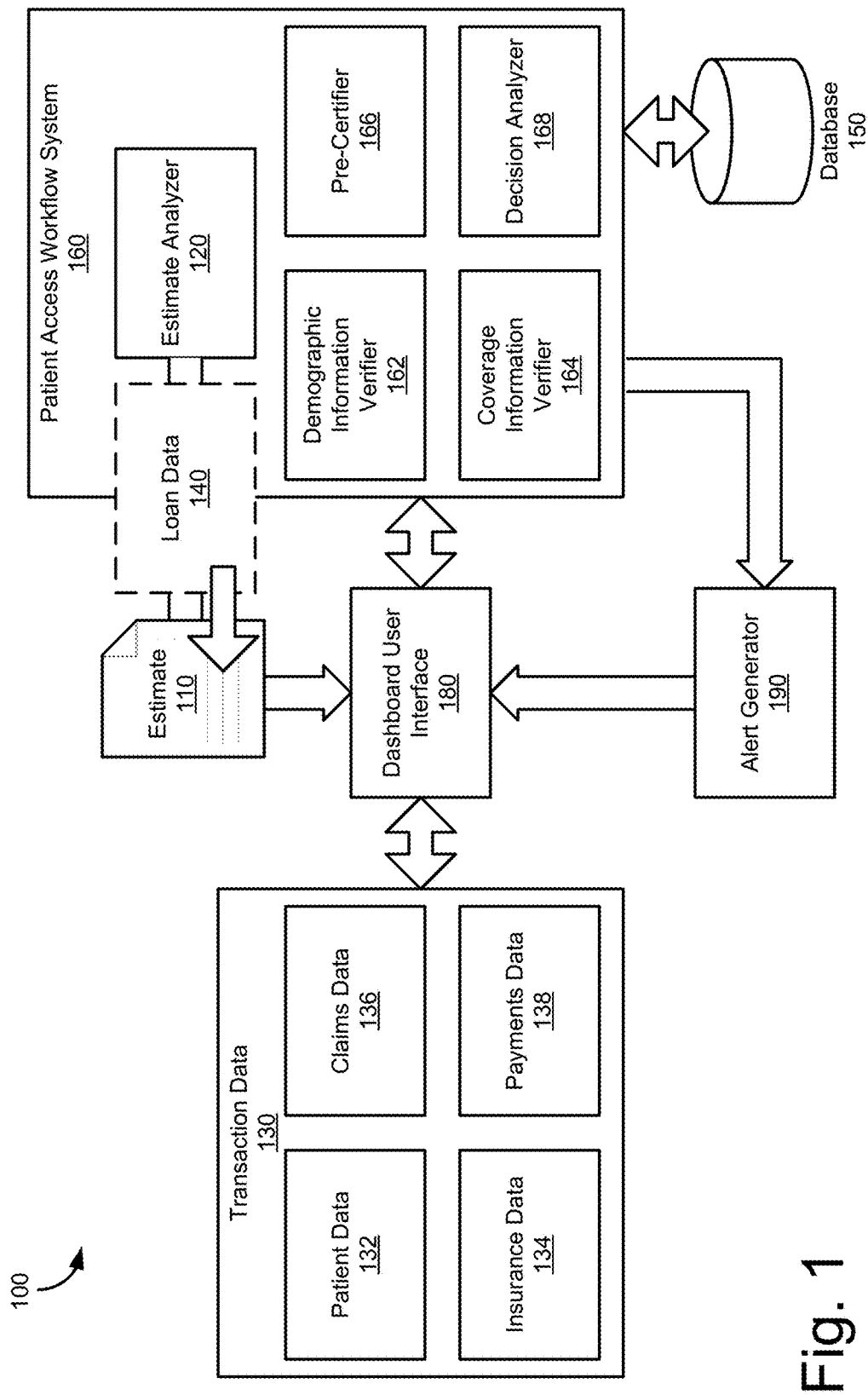
FIG. 1 is a block diagram illustrating an example service processing system operable to provide payment estimation and validation.

The following detailed description refers to the accompanying drawings. Wherever possible, the same reference numbers are used in the drawings and the following description to refer to the same or similar elements. While aspects of the present disclosure may be described, modifications, adaptations, and other implementations are possible. For example, substitutions, additions, or modifications may be made to the elements illustrated in the drawings, and the methods described herein may be modified by substituting, reordering, or adding stages to the disclosed methods. Accordingly, the following detailed description does not limit the present disclosure, but instead, the proper scope of the present disclosure is defined by the appended claims. Examples may take the form of a hardware implementation, or an entirely software implementation, or an implementation combining software and hardware aspects. The following detailed description is, therefore, not to be taken in a limiting sense.

The present disclosure provides systems and methods for improving the functionality of service access workflow systems, such as the patient access workflow systems used by healthcare providers to process patients, the client access workflow systems used by attorneys to process clients, or the student access workflow systems used by educational institutions to process students. Although examples are given herein primarily using a patient access workflow system and involving healthcare providers and patients, it will be recognized that the present disclosure is applicable to several fields where persons seeking services are faced with high costs, and the providers are faced with the difficulty of deciding whether to deny service, provide service at financial risk to themselves (or later seek to collect the debt themselves), and to reach that conclusion in a time sensitive environment. Improvements to the speed, accuracy, and capabilities of these service access workflow systems not only improve the systems themselves, but reduce the financial risks to providers in providing services and improve patient access to healthcare, client access to legal services, and student access to educational services, etc.

Due to the complex nature of paying for healthcare services, which may include multiple payors (e.g., private insurance providers, governmental insurance providers, pharmaceutical companies, charities (including write-off and discount programs), guarantors, and the patients themselves) who have negotiated for different costs for a given procedure, the estimation of costs are handled by the provider systems, which can provide results faster than a human can. Because these results are used by the parties when agreeing to a course of treatment, and the fact that rendered services do not provide a security or other object that can be repossessed in the event of a default, the rendering of a cost estimate is a time-sensitive process whose speed and accuracy are of immense importance to both patient and healthcare provider. As used herein, "accuracy" and its related adjectives and adverbs do not refer to the correctness of how calculations are preformed (which are assumed to be performed correctly, unless stated otherwise), but refer to how close an estimate is to a final value. For example, if the final value for the costs of healthcare services is $100, an estimate of $99 would be more accurate than an estimate of $98.

The present disclosure provides for an integrated system, and methods for the use thereof, that performs patient processing tasks, and aids healthcare providers in assisting patients to secure outside financing when considering courses of treatment. By helping locate outside financing before a procedure is performed, when a patient is determined to be unable afford a procedure, healthcare providers may reduce their risk of acting as a "bank" or lender for their patients' procedures, and patients may be encouraged or discouraged to undergo various procedures based on expanded information regarding the affordability of those procedures. For example, patients may forgo medically necessary procedures, such as hip or knee replacements, and choose to live with pain or reduced mobility unless they see how they might pay for those procedures prior to those procedures being performed. The financing, when provided, is tailored to the individual patient, and the patient may decide to select an option pre-procedure, forego pre-procedure financing, or select an option post-procedure.

By integrating the systems, the present disclosure increases the speed at which a patient processing system returns its results, reduces the bandwidth required to produce and communicate those results, improves upon the prior patient processing systems, and the usefulness of the technology is extended. A patient processing system that is faster, more reliable, and uses fewer communications between remote systems is thus produced, and provides both healthcare providers and patients with greater assurance that the highest quality healthcare will be provided.

Examples of numbers in the present disclosure are given in base ten unless noted otherwise. When a different base is used, a subscript beginning with the character "x" and the base value (in base ten) will follow the number. For example, the number ten may be designated as 10, $A_{x16}$, or $1010_{x2}$ for decimal, hexadecimal, and binary examples respectively. Additionally, for numbers given in binary formats, numbers will be presented in groups of four with spaces between each group. For example, the number one is presented as $0001_{x2}$ and the number seventeen is presented as $0001\ 0001_{x2}$. When individual values for bits are discussed, they may be represented as "one/TRUE" or "zero/FALSE" to distinguish these values within the text. Additionally, for purposes of clarity, numbers may be presented in examples and drawings as italicized letters (e.g., X, Y, n, m, etc.), which may represent any number, its ordinal (e.g., Xth, Yth, nth, mth, etc.), and mathematical variations based from those numbers (e.g., 2X, Y/3, n+4, (m−5)th, etc.). One of ordinary skill in the art will be able to read and understand these values within the context that they are given in the present disclosure.

FIG. 1 is a block diagram illustrating an example service processing system 100 operable to provide payment estimation and validation. The components illustrated in FIG. 1 are part of an integrated patient processing system 100, which is provided as a singular service that multiple healthcare providers may access. In various aspects, the healthcare providers may access the patient processing system 100 remotely via a thin client, which receives data from the healthcare provider and posts back results via a web browser, or a dedicated application running on a terminal or server operated by the healthcare provider used to communicate with the patient processing system 100.

When a patient seeks healthcare services from a healthcare provider, an estimate 110 is provided to the patient (or to a guarantor of the patient's account) so that an informed decision can be made regarding a course of treatment that includes the cost of that treatment. For example, a patient may be provided with two estimates 110 for alternative courses of treatment (e.g., a traditional plaster cast or a water-proof fiberglass cast for a broken bone) to select one course of treatment or to prepare the patient for the eventual costs of an already-selected course of treatment. The estimate 110 is determined by an estimate analyzer 120, which uses various information, herein referred to as transaction data 130, to determine the values in the estimate 110.

The transaction data 130 include a selection of one or more procedures anticipated to be performed, which may involve related procedures commonly performed in conjunction with the selected procedure. For example, a colonoscopy procedure may involve anesthesia, and in some cases, a biopsy, which would be included in the transaction data 130. The related procedures may be automatically provided as part of a procedure template for a selected procedure or treatment. The transaction data 130 also incorporate patient data 132 and insurance data 134. The patient data 132 include a patient's name, account number, and other demographic data, such as, for example, the patient's address, phone number(s), social security number, date of birth, gender, marital status, emergency contact information, employment status and details, student status and details, guarantor information, etc. If a guarantor of the patient's account is different than the patient (e.g., a parent-guarantor of a child-patient), the patient data 132 may also include demographic data associated with the guarantor. The insurance data 134 include information regarding the patient's insurance coverage, such as, for example: whether a patient has insurance coverage, and if so, who the insurance provider is, what type of plan the patient has, etc.

When patient data 132 are received, verifiers are triggered to apply various rules and intelligence for verifying the received patient data 132 against data in one or more databases 150. According to aspects, various requests may be sent automatically to one or more patient access workflow systems (PAWS) 160 to perform one or more patient access workflow processes. An example of a PAWS 160 would include the eCare NEXT® platform, available from EXPERIAN HEALTH, INC. of Franklin, Tenn. As one of ordinary skill in the art will appreciate, rules may be implemented via individual transistors that are discrete components of a circuit or via a processor that is configured by software to provide the corresponding logical operations necessary for comparison. These logical operations, and associated hardware, are discussed in greater detail in regard to FIGS. 5A-E.

According to one aspect, a rule may be applied to automatically send a request to a demographic information verifier 162 to cross-match a name, address, etc., of a patient or the guarantor of the patient's account (demographic information included in received patient data 132) with information stored in one or more databases 150. According to another aspect, a rule may be applied to automatically send a request to a coverage information verifier 164 to verify insurance coverages a patient (or guarantor) claims to have included in the insurance data 134. According to another embodiment, a rule may be applied to automatically send a request to a pre-certifier 166 to identify procedures that may require pre-certification according to a patient's coverage plan indicated in the insurance data 134 and available procedures stored in a database 150.

According to another embodiment, a rule may be applied to automatically send a request to a decision analyzer 168, with the consent of the patient or guarantor, to collect credit and financial information for a patient (or guarantor of the patient's account) to determine the patient's (or the patient's guarantor's) financial situation. The requests may be sent automatically; a user is not required to manually send a request to perform a patient access workflow process, although these requests may also be sent manually by a user or require patient (or guarantor) authorization before being sent. In the illustrated aspect, the decision analyzer 168 is part of the PAWS 160, but in other aspects, the decision analyzer 168 may be integrated into the estimate analyzer 120 or may be a separate system from the PAWS 160 and the estimate analyzer 120.

In various aspects, when the decision analyzer 168 determines, based on the rules and a given patient's credit information and financial information, that the patient qualifies for financing, the estimate analyzer 120 will be signaled to include loan data 140 in the estimate 110. The loan data 140 are not produced when it is determined from the patient's financial information that the patient will qualify for charity care programs. According to aspects, the determination of whether the patient qualifies for a charity care program is performed before loan data 140 are produced; saving processing resources when loan data 140 do not need to be produced. For example, the financial information may indicate the patient's income and household size, which are compared against an income threshold to determine eligibility for charity care programs offered by the government, private charities, or the healthcare provider itself for the benefit of the public. In other aspects, the loan data 140 are not produced when it is determined from the patient's financial information that the patient is able to afford the procedure without a loan. For example, if the patient does not qualify for charity care, but the costs of the procedure are deemed low enough to be affordable (e.g., below n % of the patient's yearly income), loan data 140 will not be produced.

Unlike prior art systems, where the applicants' data are loaded into a local system and transmitted to several external loan providers (e.g., banks) for further processing and subsequent transmission of terms back to the local system, the estimate analyzer 120 is operable to accept the patient's data one time and return multiple loan options from multiple lenders without transmitting multiple requests for potential loan terms to multiple loan providers each time a patient is eligible for a loan. Instead, the rules that the decision analyzer 168 uses are based on an internal risk assessment of the patient. The internal risk assessment is based on a healthcare provider specific analysis of its patient-base and its history of receiving payments from that patient-base. Data on the patient-base is used by the decision analyzer 168 to identify attributes shared by segments of the patient base with the patient, which are used to derive scores for the patient related to a risk of repayment, and a decision is made, based on the patient's scores and the preferences of the healthcare provider. For example, a hospital in city A and a hospital in city B, when presented with the same patient, may come to different conclusions on the patient's repayment risk. The patient data 132 and insurance data 134 for a given patient are compared to historic aggregated patient data 132, insurance data 134, and associated payments data 138. The payments data 138 include information related to how the charges for a procedure are scheduled for payment, and whether (and to what extent and over what time period) the payments have been received.

The risk assessment of the patient is used to pre-qualify the patient for various loans from loan providers who have contracted with the healthcare provider (or the third-party provider of the PAWS 160). When a risk assessment is calculated, the loan data 140 include the loans that the estimate analyzer 120 selects to present to the patient via the dashboard user interface (UI) 180. Because the patient is being pre-qualified via the dashboard UI 180, and not pre-approved, the loan data 140 do not represent actual loan offers from the lenders, but rather loan terms that the estimate analyzer 120 predicts to be offered by lenders for a given risk assessment and estimate 110 and previous behavior of the lenders. How the risk and rights to collect on the loan are transferred from the healthcare provider and the lender (e.g., whether the loan is a recourse or a non-recourse loan) is handled separately by the PAWS 160 with the lender selected by the patient from the dashboard UI 180, which reduces the amount of bandwidth used to present loan terms, as the patient's selection is only transmitted to the selected lender, but offers of terms from multiple lenders are provided to users. When the estimate analyzer 120 predicts that no outside lender (or fewer than a set minimum number of lenders) would be willing (at all or within ranges set by the healthcare provider) to provide terms acceptable to present an offer to service the patient's estimated debt, the healthcare provider itself will be presented as a lender with terms it sets as acceptable.

In various aspects, if the circumstances under which the loan data 140 were generated have changed (e.g., the procedure costs more than estimated, complications arose and additional procedures were required, a patient's creditworthiness changed), a lender may change the terms of the loan (or alternative lenders may be contacted) for the patient to accepts at new rates and/or principal amounts. Alternatively, the terms selected by the patient from the dashboard UI 180 may be locked in, and if the lender offers different terms to service the debt, the patient will still be provided the offered terms at either the healthcare service provider's benefit or detriment (for better or worse actual terms, respectively). The estimate analyzer 120 will periodically adjust its predictions, based on historic data, to provide more accurate estimates of loan terms.

Figure 2:
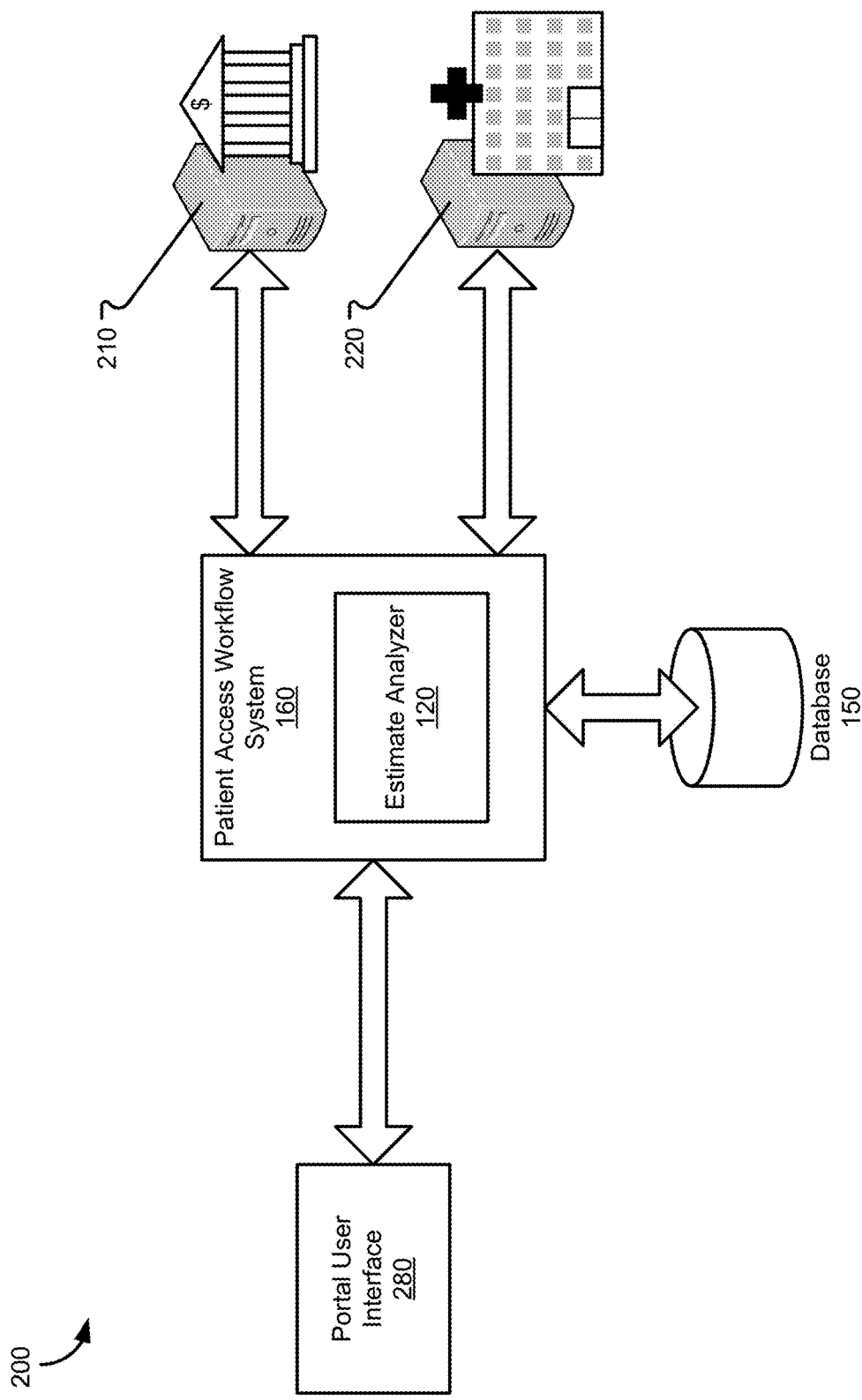
FIG. 2 is a block diagram illustrating an example service processing system operable to provide patients with a platform for post-procedure payment management in conjunction with the pre-procedure estimates.

In various aspects, the patient may select a loan from the dashboard UI 180 prior to the procedure being performed, or defer accepting a loan until after the procedure is performed, as is discussed in greater detail in regard to FIG. 2. When a loan presented in the dashboard UI 180 is accepted from the dashboard UI 180, the selection is transmitted to the PAWS 160, which will forward a tokenization of the loan data 140 to the lender to accept the terms offered by the PAWS 160 as-is, with modifications, or reject the terms. In alternate aspects, lenders provide loan terms matched to various risk profiles to the PAWS 160 (and stored in the database 150) that are matched to patient risk assessments which are provided as the tokens for the patient to select from. Tokens self-contained wrappers for the relevant data for a patient's pre-qualification that are transmittable between different systems and entities. In various aspects, a token may be for a single loan offer for a patient, or contain all the loan offers generated for a given patient. Alternatively, the lenders may provide a set number of unassigned tokens for various terms from which the PAWS 160 may select for presentation to the patient (at which point the token is assigned to the patient), and when a given token is selected, the PAWS 160 will remove that token from a pool, so that the offered loan is not presented to a subsequent patient (although a different loan with identical terms may be presented to a subsequent patient if a token with identical terms exists in the database 150).

The estimate analyzer 120 included in the PAWS 160 is further operable to compare claims data 136 and payments data 138 with a related estimate 110. The claims data 136 include information related to the final charges accrued for a procedure and any related procedure that resulted from the original procedure for which an estimate 110 was generated. For example, the estimate 110 for an examination for a broken arm may have stated that the total cost would be $800, and the patient would bear $400 of that cost (the rest being paid by insurance or discounted), while the claims data 136 indicate that the final charges were actually for $900, of which the patient owes $500, due to the need to retake X-rays and the associated costs. The payments data 138 will indicate when the $900 is due, from what parties the payments are expected (e.g., the patient, a guarantor, an insurer, written off), and whether the payments have been received.

One or more records may be associated with each estimate 110 completed by the estimate analyzer 120. The various data, the estimate 110 and any associated records thereof are stored in one or more databases 150. The databases 150 are hardware devices that comprise computer readable storage media on which these information are stored. The databases 150 store data and metadata such as patient encounter data, patient coverage data, alerts, results from one or more patient access workflow processes, and collections amounts. Erroneous or missing patient data 132 may be automatically corrected and/or one or more alerts may be provided so that correct information is supplied to remedy the erroneous or missing data. Erroneous information includes information that conflicts with information stored in the database 150 or does not match other input data. For example, if a patient provides a wrong Social Security Number (SSN) or an administrative user were to enter the SSN incorrectly, the SSN would conflict with the information stored in the database 150. Similarly, if a patient has his gender entered as "male" during intake, but the procedure selected is for "women's health services," those entered data fields will be determined to conflict. In various systems, what constitutes a conflict will be set by rules, and an administrative user, in some aspects, may be able to override some conflicts or may be compelled to correct other conflicts before proceeding with patient processing, based on rules for the conflicts.

On a periodic basis (e.g., every X minutes), or when manually invoked, the estimate analyzer 120 parses a database 150 for records of estimates 110. According to one aspect, the estimate analyzer 120 parses the database 150 for all stored estimates 110. According to another aspect, the estimate analyzer 120 parses the database 150 for estimates 110 within a selected time period (e.g., estimates 110 made within the last week, month, this month last year, etc.).

The estimates 110 are compared with claims data 136 and payments data 138 to determine the accuracy of the estimates 110 for future refinement. Results may be displayed in a user interface, for example, a dashboard UI 180 or may be used privately by the patient processing system 100 to iteratively improve the rules that govern the estimate analyzer 120. In various aspects, the dashboard UI 180 is also used by an operator to input data (e.g., patient data 132, insurance data 134, claims data 136, payments data 138) manually into the PAWS 160 at the prompting of associated data fields in the dashboard UI 180. The dashboard UI 180 may also display information to an operator that has been retrieved automatically from a database 150. For example, after a user inputs a patient's identification number, the PAWS 160 may retrieve, based on the patient identification number supplied, stored patient data 132 and insurance data 134 from a database 150, which will be used to auto-populate the dashboard UI 180.

In various aspects, the dashboard UI 180 is provided as website generated by the PAWS 160 that the healthcare provider accesses via a thin client on a local terminal. In other aspects, the dashboard UI 180 is provided by a dedicated application run by the healthcare provider on a local server or local terminal, that transmits data to the PAWS 160. The dashboard UI 180 is operable to receive data entered by the healthcare provider for provision to the PAWS 160 and to receive information from the PAWS 160 for provision to the user (e.g., administrative user, patient, etc.) of the dashboard UI 180. Further information on an example dashboard UI 180 is presented in regard to FIG. 3.

Various aspects include an alert generator 190, which is operable to generate and transmit alerts to notify a user (e.g., administrative user, patient, etc.) of potential problems (e.g., missing information, erroneous information, etc.) or additional steps needed to be completed for performing one or more processes of a patient access workflow. Providing alerts of potential problems or additional steps may provide for an exception-based workflow where a user addresses and prioritizes patient accounts with potential problems or accounts needing the attention of a user. Accordingly, the user may be able to solve identified problems proactively. The alert generator 190 sends alerts via post back to a web browser or via signal to a dedicated application, depending on how the healthcare provider accesses the patient processing system 100. In various aspects, the alerts are generated in the dashboard UI 180 for display in proximity to the data fields for which the alert was generated.

FIG. 2 is a block diagram illustrating an example service processing system 200 operable to provide patients with a platform for post-procedure payment management in conjunction with the pre-procedure estimates. The patient accesses the post-procedure processing system 200 via a portal UI 280, which may be provided on a computer device owned by the patient or a computer device provided by the healthcare provider or a third party. In various aspects, the portal UI 280 is a thin client provided by a web browser that remotely accesses the PAWS 160 over a network, such as, for example, the Internet or an intranet. The PAWS 160 is in communication with a banking system 210, a healthcare provider system 220, and a database 150 to coordinate the payment process. As will be appreciated, more than one portal UI 280 may be provided, to connect different entities (lenders or healthcare providers) and the patient, so as to provide customized display interfaces and use Application Program Interfaces (API) specific to the systems used by the entities to which the portal UI 280 connects.

In various aspects, the patient may access the PAWS 160 via the portal UI 280 to manage loans that have already been accepted, to apply for loans for procedures that have already been performed using loan data 140 generated before the procedure, or to apply for a loan for a procedure that has already been performed without using loan data 140 generated before the procedure.

When loan data 140 are generated prior to the procedure, but the patient defers on applying for any of the presented options in the dashboard UI 180, the loan data 140 are saved as tokens within the PAWS 160. In various aspects, the tokens include the original loan data 140 for the offers, the patient risk assessment determined by the PAWS 160, an expiration date for the offers, and/or modification data, and include data on each of the presented sets of terms which are stored by the PAWS 160 so that the terms may be re-presented to the patient after the procedure via the portal UI 280. The tokens are transmitted to the computer device used to present the portal UI 180 to enable the patient to select from the offers, post-procedure. As will be appreciated, the circumstances under which the offers were originally made may have changed between pre-procedure offering and the post-procedure display (e.g., the procedure cost more than estimated, complication arose and addition procedures were necessarily performed, the patient's (or guarantor's) credit-worthiness changed), therefore the portal UI 280 is operable to display the current terms of the offer, modified by modification data included in the token. For example, if the actual cost of the procedures exceed a difference threshold from the estimated costs of the procedures, then the lender may adjust the terms of the loan (for the patient's approval) or decline offering the loan as originally presented pre-procedure. In another example, if the offer were based off of the Federal Funds Rate (FFR), and the FFR were to change between pre-procedure and post-procedure, the offer re-presented by the token would be adjusted accordingly. Similarly, when an expiration date is included in the token, the token may be automatically deleted from the PAWS 160 when the expiration date is passed, and that offer will no longer be presented to the patient in the portal UI 280.

When the patient selects a particular loan and chooses to apply for it via the portal UI 280, the PAWS 160 transmits the loan's token to the banking system 210 of the lender with which it is associated. Based on the loan data 140 and the terms in the token, the offer may be accepted as-is, modified, or rejected by the lender. Depending on the differences between the terms in the token and the terms set by the lender, the healthcare provider may present the altered terms to the patient for final approval, alter its terms with the lender so that the lender will offer terms identical to what were originally presented to the patient (e.g., entice the lender to provide the terms as-offered to the patient), or an alternate lender (including the healthcare provider itself) may be sought to provide terms as originally offered to the patient. When the lender's terms and the originally offered terms differ, the estimate analyzer 120 will use the difference to adjust how it provides estimates in the future from the corresponding lender, for example, by a machine learning approach (Q-learning, Analysis of Variance (ANOVA), State Action Reward State Action (SARSA), etc.).

In various aspects, the banking system 210 may transfer funds for debt sale or acceptance of servicing the loan to the healthcare provider's financial institution, directly to the healthcare provider system 220, or via the PAWS 160 to the healthcare provider system 220. In various aspects, tokens may be presented to lenders individually or in bundles, and bundles may be group via categories to include only pre-procedure acceptances, only post-procedure acceptance, pre- and post-procedure acceptances, various risk assessments, various amounts, and combinations thereof.

When the patient makes a payment via the portal UI 280, the PAWS 160 receives the payment authorization from the portal UI 280. As will be appreciated, payment authorization may include a Bank Identification Number (BIN) or an Issuer Identification Number (IIN) for an account used to make a payment, an account number, an amount of payment, a desired date of transaction so that the authorized payment may be made. Additionally, the PAWS 160 may transmit data the healthcare provider system 220 to update payments data 138, or track payments data 138 locally, (specifically for a patient or anonymously in aggregate for a patient-base) to provide historical data on payments to improve the accuracy of the estimate analyzer 120 in generating a risk assessment for a patient. These payments data 138, when collected, are stored in the database 150, and may be accessed by the patient via the portal UI 280 to view historic transactions.

FIG. 3 illustrates an example dashboard UI 180 as would be seen by a user during a pre-procedure price estimation phase. As will be appreciated, other configurations than those illustrated in FIG. 3 are possible, and FIG. 3 is provided as a non-limiting example of a dashboard UI 180. Illustrated in FIG. 3 are several data fields (including data), controls, and instructions for completing the price estimation phase. As will be appreciated, the dashboard UI 180 will provide different data fields, data, controls, and instructions during other phases of processing a patient. For example, during a demographics phase, data, data fields, controls, and instructions related to the input and presentation of patient data 132 will be presented in the dashboard UI 180, such as, for example: data fields for inputting names, addresses, dates of birth, etc.; instructions for how to fill the data fields; and controls to submit the data input in the data fields to the PAWS 160.

The dashboard UI 180 includes a navigation pane 310 that includes information regarding a given patient, the current phase or status of patient processing, and navigation controls, operable to move the dashboard UI 180 to different phases of patient processing and/or to different patients. In various aspects, the navigation controls include directional buttons (e.g., Previous or Next) for navigating to a previous/next patient or a previous/next phase in an ordered list of patients or phases. In other aspects, the navigation controls include tabs, displaying all (or a displayable subset) of the available patients or phases, from which a user may select. In yet other aspects, a search feature will be included with the navigation controls so that a user may type all or a portion of a name for a patient or phase and navigate to that patient or phase. As will be appreciated, the navigation controls may be implemented to limit navigation based on context. For example, in a first phase of an ordered list of phases, a "Previous" navigation control will not be provided, not be selectable, or will be "grayed out." In another example, a patient who is scheduled for a 10:00 am appointment may not be navigable to until 9:30 am or after a predetermined time after the appointment (e.g., two hours, thirty minutes, one month, etc.) to reduce the number of navigable patients a user may be presented with, and the computational load of the system providing the dashboard UI 180.

In the estimate phase, the dashboard UI 180 includes procedure selection summaries 320, which are controls that include information provided by the estimate 110 regarding procedures available to the patient. The controls are selectable and modifiable by a user so that multiple alternate courses of treatment may be examined, for example, using a plaster cast versus a fiberglass cast to treat a broken bone. Additionally, related sub-procedures may be broken out as separate procedure selection summaries 320, such as, for example, providing casting procedures separately from X-ray procedures for the treatment of a broken bone, to provide greater detail in the billing process for a course of treatment. A user may manipulate the controls to dismiss unwanted options (e.g., by hitting an "X" sub-control, or the like) or to change a number of times a procedure is to be performed. In various aspects, an unwanted procedure may be retained, but have its number of times to be performed set to zero, or a procedure that is desired to be performed n times, will have that its number of times to be performed set to n, and the estimated costs will be adjusted accordingly. When a number of times a procedure is to be performed is set to zero, the associated procedure selection summary 320 may be grayed out, or another visual indicator may be applied to the procedure selection summary 320 to indicate that it is not being applied to the cost tabulation for the course of treatment.

Once procedures are selected during the estimate phase, it may be determined that the patient is eligible for financing, in which case financing input 330 will be presented via the dashboard UI 180. The financing input 330 includes instructions for the user for how to ask for financing and may include data fields by which the user may modify patient data 132, either globally in the dashboard UI 180 or limited to purposes of finding financing (e.g., prior addresses may be requested).

As will be appreciated, for a patient to be provided financing options, the patient must provide approval to have their patient data 132 potentially shared with financial institutions. The dashboard UI 180 therefore includes authorization controls 340 when financing is available to the patient so that the user of the dashboard UI 180 can receive the patient's approval (or the patient's denial of approval) to pursue financing. For example, the dashboard UI 180 includes a denial-of-authorization control 340 (a negative control) to note that the patient does not approve of seeking financing during the estimate phase and has denied authorization to share patient data 132. In an example of positive controls, a verbal authorization control 340 may be provided to make use of a microphone included in a terminal providing the dashboard UI 180 to receive a voiced approval from the patient. In another example, a written authorization control 340 may be provided to make use of a touchscreen, touchpad, or camera included in a terminal providing the dashboard UI 180 to receive a signature or biometric marker (thumbprint, vein pattern, etc.) indicating authorization from the patient.

When approval to seek financing during the estimate phase is received (e.g., by actuating positive authorization controls 340), the dashboard UI 180 may provide a popup dialog to receive the patient's authorization. Once the patient's authorization (or denial) is received, the authorization will be stored, for example, in the database 150, with the records for the encounter with the patient (as a sound file of voiced approval, an image file of written approval, etc.), and the estimate analyzer 120 will provide loan data 140 to the dashboard UI 180. In various aspects, the authorization will be associated with (or included in) a token for an offer when the patient applies for the offer associated with the token.

The loan data 140 are presented in the dashboard UI 180 for the patient to select whether to accept any of the offers for financing, before the healthcare provider performs the procedures. The dashboard UI 180 may present a first set of loan data 140 from a first potential lender in first loan summary control 350*a* (generally, loan summary control 350) and a second set of loan data 140 from a second potential lender in second loan summary control 350*b*. Although two loan summary controls 350 are illustrated in FIG. 3, one of ordinary skill in the art will appreciate that more or fewer loan summary controls 350 may be provided.

The healthcare provider may set preferences for a maximum number of loan summary controls 350 to be presented at one time in the dashboard UI 180, for example, so that only n out of N loan summary controls 350 are presented at one time. Which of the n loan summary controls 350 are presented when N exceeds n may be controlled based on time of response (e.g., first received, first shown), a time of expiration (e.g., an offer valid for n days will be presented before an offer valued for (n+1) days), a favored status for a given potential lender (e.g., Bank A has a higher preference than Bank B and will be displayed before Bank B if a choice needs to be made as to whose loan data 140 will be displayed), a total amount charged (e.g., offers for financing with lower total charges for serving the loan will be displayed before those with higher total charges), or via another rule set by the healthcare provider.

The healthcare provider may also provide a loan summary control 350 for the terms of financing that it will offer on its own to the patient. In various aspects, a loan summary control 350 reflecting financing from the healthcare provider is only provided when no (or fewer than a set preference) outside loan providers are willing to provide financing for a procedure to the patient.

The loan summary controls 350 present loan data 140 for a given potential loan in an easily understood format.

Various aspects of the loan data 140 may be highlighted, combined, or omitted to affect its presentation. A loan summary control 350 includes functionality to allow a user to select the loan represented by a given loan summary control 350, such as, for example, radio buttons, check boxes, toggles, etc. A patient may decide to apply (or forego applying) for a loan represented by a selected loan summary control 350 via an affirmation control 360. In some aspects, when a positive affirmation control 360 (e.g., "Apply", "Accept", etc.) is selected, the terms selected by the patient are transmitted to the PAWS 160, and a loan is applied for with a lender for the terms presented to the patient at a kiosk or terminal supplied by the healthcare provider after the procedure. In other aspects, when a positive affirmation control 360 is selected, the offer will be held for the patients to later apply for on their own, for example via the portal UI 280 or by an approval packet sent via email or the postal service. When a negative affirmation control 360 (e.g., "Defer", "Cancel", etc.) is selected, the estimation phase ends without a transmission to the PAWS 160, but, in some aspects, tokens include data on each of the presented sets of terms are stored by the PAWS 160 so that the terms may be re-presented to the patient after the procedure, for example, via a portal UI 280, an example of which is discussed in regard to FIG. 4.

Also illustrated in the dashboard UI 180 are various alert icons 370. The alert icons 370 are generated by the dashboard UI 180 in response to alerts transmitted from the alert generator 190, to draw the user's attention to potential problems or next steps in patient processing. In various aspects, the alert icons 370 may be applied to various regions, data fields, data, instructions, or controls to illustrate a problem or next step for a user to take. As will be appreciated, although illustrated as an exclamation point icon, alert icons 370 may take various forms and sizes, and may be animated or include sound alerts to draw the user's attention. The alert icons 370 illustrated in FIG. 3 are therefore to be understood to be non-limiting examples of alert icons 370.

FIG. 4 illustrates an example portal UI 280 as would be seen by a patient post-procedure. Illustrated in FIG. 4 are several data fields (including data), controls, and instructions for managing the repayment for procedures. The example portal UI 280 includes several sections in which related information are presented and user interaction activities are grouped for the convenience of the patient. As will be appreciated, other configurations than those illustrated in FIG. 4 are possible, and FIG. 4 is provided as a non-limiting example of a portal UI 280.

The example portal UI 280 includes an overview section 410, providing information and controls related to the overview of the patient's account. For example, the illustrated overview section 410 includes support information, by which the patient may email or live chat a support technician (human or artificial intelligence) and a telephone number to call for assistance. The illustrated overview section 410 also includes patient account information (e.g., an account number, username, patient name), and controls to log the patient out of the portal or change preferences for the portal UI 280 (e.g., a password, contact information, payment settings, colorblind mode, font size, arrangement of sections, etc.).

The procedure section 420 presents information about a procedure that is currently selected for payment servicing by the patient. As illustrated, the information includes who performed the procedure (or aspect thereof), whether financing has been secured (and with whom and the terms thereof), and to what extent the patient still owes for the procedure.

In various aspects, when multiple parties submit bills related to one procedure (e.g., a hospital and an ambulance service, a surgery department and a radiology department), different billing and loan information may be presented in the procedure section 420, or the information may be presented as sub-items.

The service section 430 enables the patient to make payments for a selected procedure that is displayed in the procedure section 420. As illustrated, controls for setting when a payment is made, an amount of the payment, a source of the payment, and for submitting the payment are provided in the service section 430. The illustrated controls include radio buttons, drop down menus, and text fields, although other input controls may be provided, including calendar selectors, check boxes, slider bars, rotary controls, etc. Upon section of a control in the service section 430, the portal UI 280 may provide a popup, overlay, or new window to confirm selection of a control, request additional information, or process the command from the patient.

The history section 440 provides an account or procedure history to the patient. The history section 440 displays a summary of transactions associated with a patient's account, whether for a given procedure or all procedures associated with the patient's account. The procedure histories shown in the history section 440 may have been performed by different healthcare providers who subscribe to the PAWS 160 and who receive financing from different lenders. Each line item in the history section 440 may include information related to what the line item entails, what credits or debits have been applied (and in whose favor), when an action was performed, and hyperlinks to additional information related to the line item, which may be stored in a database 150 for retrieval in response to receiving a selection of the hyperlink.

A procedure selection section 450 displays different procedures that the patient can select from for display in the procedure section 420, service section 430, and history section 440. The procedures displayed in the procedure selection section 450 may include procedures that have been fully paid for, procedures for which a loan is active, and procedures for which no loan has been applied. For example, a patient may have been pre-qualified during a price estimation phase before a procedure is performed, but declined to accept any of the loans displayed in the dashboard UI 180, or may have declined to seek a loan before the procedure was performed. In various aspects, controls are displayed along with information about the procedures (e.g., active, available, or completed loans) to enable the patient to select the loans associated with the procedure (for procedures with active loans), to apply for loans for a procedure whose balance is still outstanding (for procedures with available loans), and to view any historic data for procedures whose balance is settled (for procedures with completed loans).

Within the procedure selection section 450, any procedures with outstanding balances that do not have a loan associated with those balances may include controls to select loans that were previously presented to the patient via the dashboard UI 180 before the procedure was performed. The original terms may be communicated to the portal UI 280 via tokens, sent when the patient deferred accepting a loan prior to treatment. In various aspects, the tokens include the original loan data 140 for the offers, an expiration date for the offers, and/or modification data. For example, if the loan data 140 were offered when the procedure was estimated to cost m dollars, but the patient seeks to accept a loan after the procedure actually cost n dollars, the modification data may set whether the offer is still valid or if the offer should be modified to reflect the change from m to n dollars. Offers whose tokens have expired, or that have been invalidated by the modification data, are not displayed in the procedure selection segment (and, in some aspects, delete themselves from the PAWS 160), whereas offers that have not expired, or have been modified according to the modification data, will be displayed accordingly. As will be appreciated, some or all of the tokens for offers that were presented in the dashboard UI 180, or tokens for offers that were not displayed in the dashboard UI 180 (e.g., due to space constraints of healthcare provider preferences), may be displayed in the procedure selection section 450, and the number and selection of offers displayed may be limited by patient preferences.

As will be appreciated, each of the sections may be presented in a separate sub-window that takes up a pre-set amount of space within the portal UI 280 so that if the amount of information or controls in one of sub-windows exceeds the display capacity of the sub-window a scroll bar may be provided to enable the patient to navigate the contents of that section individually without affecting the display of the rest of the sections or the portal UI 280 as a whole. Alternatively, as each of the sections grows to contain more information or controls, more of the portal UI 280 will be devoted to displaying the sections, and a scroll bar may be provided to enable the patient to navigate the contents of the portal UI 280 when it exceeds the viewing area of a web browser window or monitor.

FIGS. 5A-E illustrate various circuit diagrams for circuits applicable to digital devices, such as an estimate analyzer 120, operable to perform various rules and comparisons as part of the systems and devices of the present disclosure. As illustrated in FIGS. 5A-E, bits from a first data source are labeled with an "a" and bits from a second data source are labeled with a "b" so that their source may be readily apparent. First input bits 511 and nth input bits 512 correspond to different bits on which data are encoded, comprising the data from the first and second data sources being compared, such that first input bit 511*a* and nth input bit 512*a* are from the first data source, and first input bit 511*b* and nth input bit 512*b* are from the second data source.

The circuits are sized to accommodate the largest possible data field from the PAWS 160. For example, when a data field contains a maximum of twelve characters, each character being encoded in one byte (e.g., according to ASCII or a basic Latin set from the UTF-8 standard), the logic gate array will accept up to 192 inputs (i.e., 12*8*2 inputs). When the data within a data field do not fully fill that data field, such as when only twelve characters are encoded in a field with a maximum size of thirteen characters, any unused bits may be set to zero/FALSE or no input to the corresponding leads of a given logic gate array will provided.

An arrayed logic gate will accept multiple inputs to produce a single output per the rules of the logic gate. For example, an AND logic gate array 520 will accept n inputs and produce one output, wherein than one output will return zero/FALSE unless all of the n inputs are one/TRUE, in which case it will return one/TRUE. In another example, an OR logic gate array 530 will accept n inputs and will produce one output, wherein that one output will return one/TRUE if any of the n inputs is one/TRUE, otherwise the logic gate array will return zero/FALSE. One of ordinary skill in the art will be familiar with the truth tables of different logic gate arrays. One of ordinary skill in the art will also be familiar with the construction of logic gate arrays from various transistors (e.g., Bipolar Junction (BJT), Field Effect (FET), etc.), diodes, resistors, memristors, and combinations thereof that are stand-alone electrical components, part of an integrated circuit, or provided by a processor.

As will be appreciated, a rule may make multiple uses of one or more of the example circuits to provide greater nuance in comparisons between data sources. For example, multiple existence checks may be performed against a rule definition to determine whether an input falls outside of a range (or falls within a category of a plurality of categories). The multiple outputs from these circuits may be combined via AND or OR operations to return a passing state or a failing state of the rule. Alternatively, when only one circuit is used, its output's state may be used to return a passing or failing state of the rule.

Figure 5A:
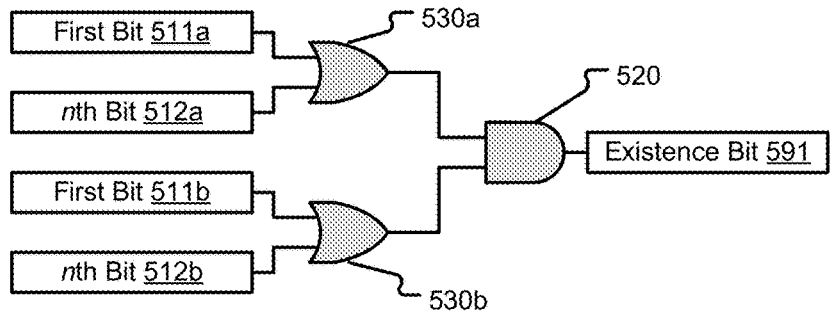
FIGS. 5A-E illustrate various circuit diagrams for circuits operable to perform various rules and comparisons.

FIG. 5A is an example diagram of an existence circuit 501 corresponding to a rule for comparing whether data exist in a data input. As illustrated, each of the bits are input into an OR logic gate array 530. First input bit 511*a* through nth input bit 512*a* from the first data source are fed into a first OR logic gate array 530*a*, and first input bit 511*b* through nth input bit 512*b* from the second data source are fed into a second OR logic gate array 530*b*. The output of the first OR logic gate array 530*a* is then combined with the output of the second OR logic gate array 530*b* via an AND logic gate array 520 to produce an existence bit 591 to indicate that the data from the first and second data sources exist, as defined by each other, with a one/TRUE value, or one does not exist with a zero/FALSE value. As will be appreciated, if the first data source represents a rule definition that is known to exist, the first OR logic gate array 530*a* may be replaced with a one/TRUE value input to reduce the number of logic gate arrays required.

Figure 5B:
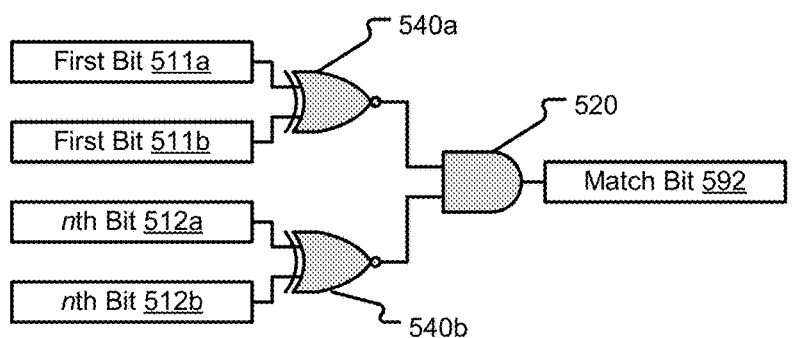

FIG. 5B is an example diagram for a matching circuit 502 corresponding to a rule for comparing whether the data from the first and second data sources match. Each bit from the first data source is combined with the corresponding bit from the second data source via an XNOR logic gate array 540. For example, a first input bit 511*a* from a rule definition will be XNORed with a first input bit 511*b* from patient data 132 via a first XNOR logic gate array 540*a*, and an nth input bit 512*a* from a rule definition will be XNORed with an nth input bit 512*b* from the patient data 132 via an nth XNOR logic gate array 540*b*. The output of the first XNOR logic gate array 540*a* is then combined with the output of the nth XNOR logic gate array 540*b* via an AND logic gate array 520 to produce a match bit 592 to indicate a match with a one/TRUE value, or no match with a zero/FALSE value.

A rule may allow for inexact matches as well as exact matches. Therefore, the input bits to the matching circuit 502 may be substituted or discarded from consideration via bit shifting or ignoring portions of the data to be compared. For example, input data for a personal name may be "DOE JOHN", whereas a rule definition for a name may have "DOE JOHN Q", and the bits used to encode the extra "Q", which are not found in the input data, may be ignored so that the data may be considered to be matching. Similarly, if a different rule definition used the name value "DOE JONATHAN", the term "JONATHAN" could be recognized by a separate matching circuit 502 so that the term "JOHN" may be substituted for "JONATHAN" when comparing the data, so that an inexact match will return one/TRUE. The separate circuits for exact and inexact matches may be combined via an OR gate to provide a single output for a configuration.

Figure 5C:
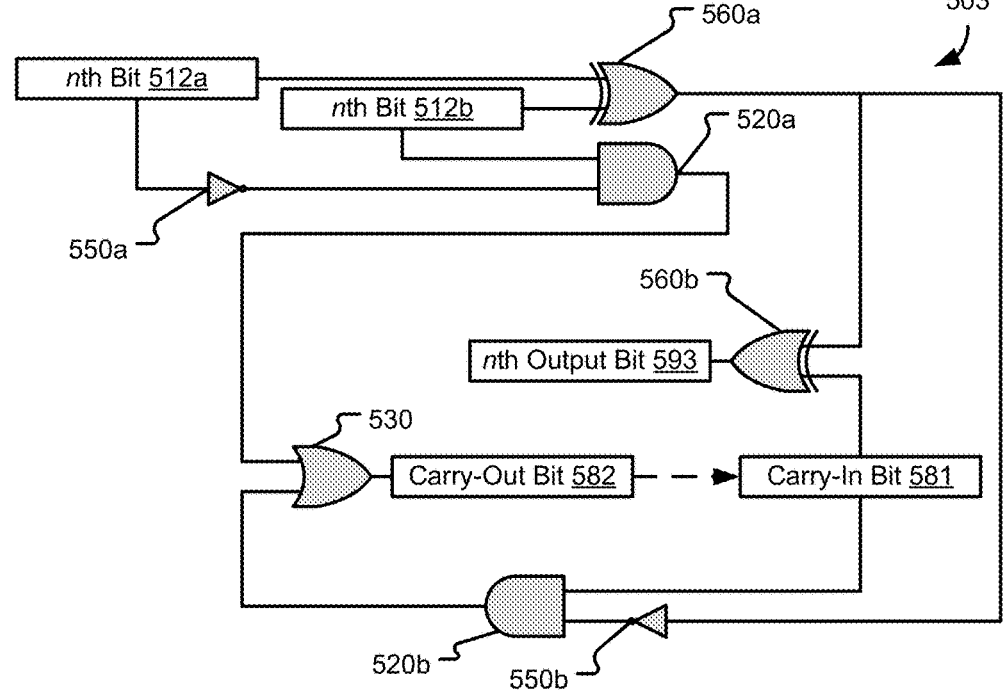

FIG. 5C is an example diagram for a bitwise subtractor circuit 503 corresponding to a rule for finding the difference between two sets of data. In various aspects, before subtracting one set of data from another, the values of those data are converted from character representations of digits of that number (e.g., in the UTF-8 or ASCII formats) to a binary representation of that number. For example, the number twelve in UTF-8 format is represented as two characters (i.e., "1" and "2"), each with its own encoding for the digit it represents (0011 0001$_{x2}$ and 0011 0010$_{x2}$, respectively), whereas the number twelve in binary notation is represented as 0000 1100$_{x2}$. As will be understood, there are multiple ways to represent a number in a binary format that account for negative and fractional numbers, and the precise format may vary in different aspects so long as the number is represented as a whole and not via individual representations of the digits.

As will be recognized, bitwise subtraction operations include inputs bits for a minuend, a subtrahend, and a carry-in, and produce outputs bits for a difference and a carry-out. The minuend is the input from which the subtrahend is subtracted, which are illustrated as the nth input bit 512a from the first data source and the nth input bit 512b from the second data source respectively.

A carry-in bit 581 represents "carry-over" from a previous bitwise subtraction operation (e.g., from the (n−1)th bits from the two data sources) and a carry-out bit 582 represents "carry-over" from the current operation to the next bitwise subtraction operation (e.g., for the (n+1)th bits from the two data sources). The carry-in bit 581 for the first bits subtracted will be zero/FALSE, but for any subsequent bits will be equal to the carry-out bit 582 from the previous bits' operation. Thus, for subtraction of numbers represented n bits, n or more bitwise subtractor circuits 503 are chained together by their carry-in bits 581 and carry-out bits 582, and the chain begins with the least significant bits representing the two numbers.

In the example diagram, the value of the carry-out bit 582 is determined via an OR logic gate array 530, which takes its inputs from the outputs of a first AND logic gate array 520a and a second AND logic gate array 520b. The first AND logic gate array 520a uses the subtrahend and an inversion of the minuend's value, via first inverter 550a, as inputs for an AND operation. The second AND logic gate array 520b uses the carry-in bit 581 and an inversion, via second inverter 550b, of a XORing, via first XOR logic gate array 560a, of the minuend and the subtrahend as inputs for an AND operation.

In the example diagram, the minuend is XORed with the subtrahend via the first XOR logic gate array 560a, which is in turn XORed with the carry-in bit 581 via the second XOR logic gate array 560b to produce the nth output bit 593. The carry-in bit 581 is equal to the carry-out bit 582 for the previous subtraction operation. Each operation of the bitwise subtractor circuit 503 results in one output bit 593, and the output bits 593 are assembled into the difference between the numbers from the two structured sets of data in order from least significant bit to most significant bit. For example, for the operation of four (0100$_{x2}$) minus two (0010$_{x2}$), the first output bit 593 would be zero/FALSE and the second output bit 593 would be one/TRUE to yield the difference of two (0010$_{x2}$) with zero/FALSE in the least significant position and one/TRUE in the next most significant position based on the order of output from the example bitwise subtractor circuit 503.

In various aspects, a series of subtractor circuits 503 are used in combination with an existence circuit 501 to determine whether a value exceeds the bounds of a threshold rule. For example, for determining whether a value is greater than a threshold, a series of subtractor circuits 503 will be used subtract a threshold from a value, and the result is checked via an existence circuit 501 to see if the result has a positive value, indicating that the value is greater than the threshold. In an alternative example, for determining whether a value is less than a threshold, series of subtractor circuits 503 will be used to subtract the value from the threshold, and the result is checked via an existence circuit 501 to see if the result has a positive value, indicating that the value is less than the threshold. As will be appreciated, depending on how negative and positive values are tracked, a bit used to indicate sign (i.e., positive or negative), may be ignored by the existence circuit 501 in the above examples.

Figure 5D:
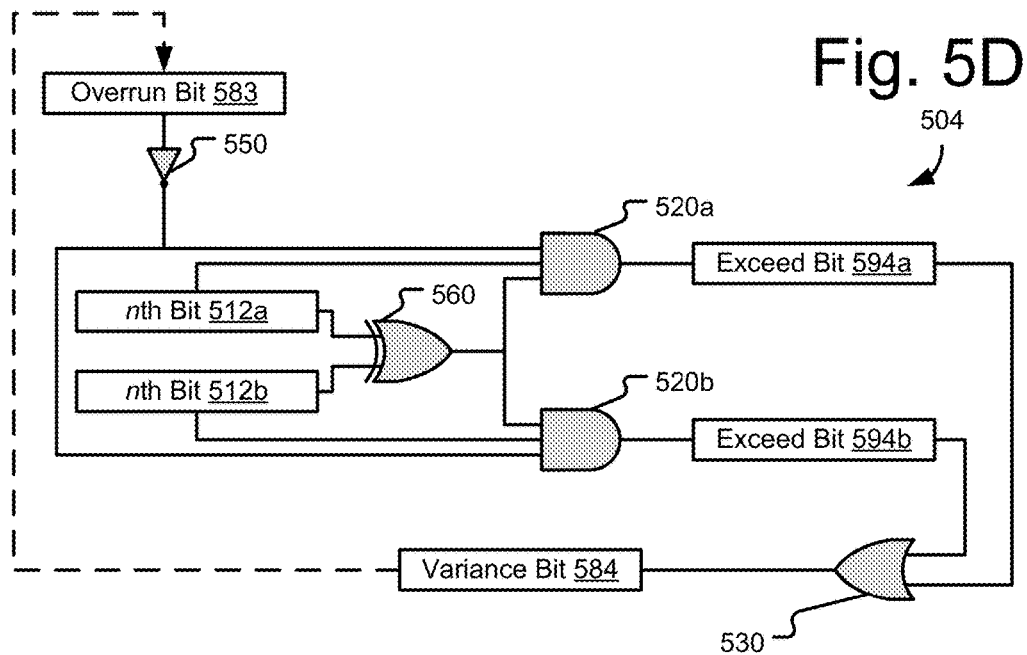

FIG. 5D is an example diagram for a bitwise sizing circuit 504 corresponding to a rule for finding which of two sets of data has the greater (or lesser) value. A sizing circuit 504 may be used to determine whether input from a first data source exceeds input from a second data source. Similarly to a subtractor circuit 503, the values of these data are converted from character representations of digits of a number to a binary representation of that number as a whole before inputting those data to the sizing circuit 504. As will be understood, there are multiple ways to represent a number in a binary format that account for negative and fractional numbers, and the precise format may vary in different aspects so long as the number is represented as a whole and not via individual representations of the digits.

As will be recognized, bitwise sizing operations include inputs bits for the data sources to compare and an overrun, and produce outputs bits for indicating whether one data or the other is greater than the other and a variance. The inputs from the data sources are illustrated as the nth input bit 512a from the first data source and the nth input bit 512b from the second data source respectively.

An overrun bit 583 represents "carry-over" from a previous bitwise sizing operation (e.g., from the (n−1)th bits from the two data sources) and a variance bit 584 represents "carry-over" from the current operation to the next bitwise sizing operation (e.g., to the (n+1)th bits from the two data sources). The overrun bit 583 for the first bits sized will be zero/FALSE, but for any subsequent bits will be equal to the variance bit 584 from the previous bits' operation. Thus, for sizing numbers represented n bits, n or more bitwise sizing circuits 504 are chained together by their overrun bits 583 and variance bits 584, and the chain begins with the most significant bits representing the two numbers. As will be appreciated, if a given number includes fewer bits in its representation than another number, it will be padded with leading zeros so that the comparison of most significant bits will compare the same values, accounting for any bits used for designating negative/positive values (e.g., when comparing binary five (0101$_{x2}$) to binary twenty-five (0001 1001$_{x2}$), binary five may be padded to be represented as 0000 0101$_{x2}$ for a bitwise comparison with twenty-five).

In the example diagram, each exceed bit 594 represents whether the associated nth input bit 512 is larger than the nth input bit 512 from the other data source. For example, first exceed bit 594a will be one/TRUE when first nth input bit 512a, associated with the first data source, exceeds second nth input bit 512b, which is associated with the second data source. Similarly, second exceed bit 594b will be one/TRUE when second nth input bit 512b exceeds first nth input bit 512a. A given bit exceeds another bit when the given bit is equal to one/TRUE and the other bit is equal to zero/FALSE.

Starting with the most significant bits, nth input bit 512a is compared with nth input bit 512b via an XOR logic gate array 560, the result of which is input to first AND logic gate array 520a and second AND logic gate array 520b. Each of the AND logic gate arrays 520 also accept an inversion of the overrun bit 583, produced by inverter 550, and the associated nth input bit 512 as inputs. First AND logic gate array 520a produces exceed bit 594a to indicate that nth input bit 512a exceeds nth input bit 512b, and that no data source in a previous iteration was determined to exceed the other by setting exceed bit 594a to one/TRUE, and otherwise setting it to zero/FALSE. Second AND logic gate array 520b produces exceed bit 594b to indicate that nth input bit 512b exceeds nth input bit 512a, and that no data source in a previous iteration was determined to exceed the other by setting exceed bit 594b to one/TRUE, and otherwise setting it to zero/FALSE.

To ensure that the sizing circuit 504 tracks whether bits of greater significance from the data sources have already determined that one dataset is greater than the other, the first exceed bit 594a and the second exceed bit 594b are combined via an OR logic gate array 530 to produce the variance bit 584. The value of the variance bit 584 is used as the value for the overrun bit 583 for the next-most significant bit to be compared by the sizing circuits 504 in the series.

When the data from the first and second data sources are equal, the exceed bits 594a, 594b will all produce zero/FALSE, but when the data from one data source exceeds the other's data (i.e., has a higher value), the associated exceed bit 594 from the first iteration of the chain of sizing circuits 504 that determines that one set of data exceeds the other will produce one/TRUE and all other exceed bits 594 will produce zero/FALSE. As will be appreciated, each of the first exceed bits 594a and second exceed bits 594b may be aggregated and combined via associated aggregating OR logic gate arrays 530 (not illustrated; one for all the first exceed bits 594a and one for all the second exceed bits 594b) between each iteration of the sizing circuit 504 for a single determination to be provided. Alternatively, each iteration of the sizing circuit 504 in a chain of sizing circuits 504 may write to the same bit, if the variance bit 584 enables a breakout from the series of circuits, in which case the overrun bit 583, inverter 550, and supporting circuitry may be omitted.

Figure 5E:
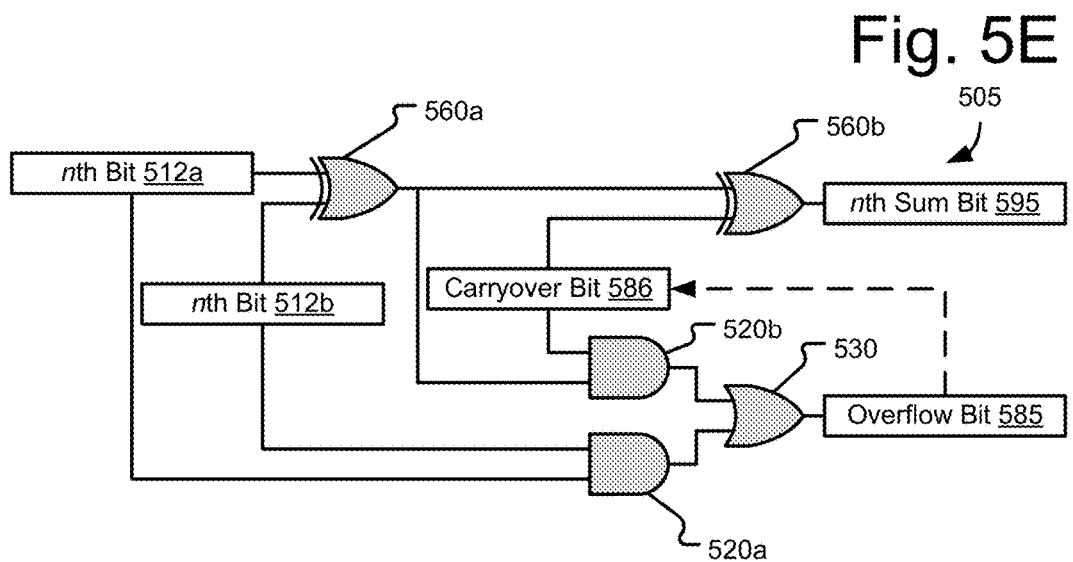

FIG. 5E is an example diagram for a bitwise full-adder circuit 505 corresponding to a rule for finding the sum of two sets of data. Similarly to subtractor circuits 503 and sizing circuits 504, the values of these data are converted from character representations of digits of a number to a binary representation of that number as a whole before inputting those data to the full-adder circuit 505. As will be understood, there are multiple ways to represent a number in a binary format that account for negative and fractional numbers, and the precise format may vary in different aspects so long as the number is represented as a whole and not via individual representations of the digits.

As will be recognized, bitwise addition operations include inputs bits for the terms to be added and a carryover, and produce outputs bits for a sum and an overflow. The terms are the bits from the data sources, which are illustrated as the nth input bit 512a from the first data source and the nth input bit 512b from the second data source respectively.

A carryover bit 586 represents "carry-over" from a previous bitwise addition operation (e.g., from the (n−1)th bits from the two data sources) and an overflow bit 585 represents "carry-over" from the current operation to the next bitwise addition operation (e.g., for the (n+1)th bits from the two data sources). The carryover bit 586 for the first bits added will be zero/FALSE, but for any subsequent bits will be equal to the overflow bit 585 from the previous bits' operation. Thus, for addition of numbers represented n bits, n or more bitwise full-adder circuits 505 are chained together by their carryover bits 586 and overflow bits 585, and the chain begins with the least significant bits representing the two numbers, which is referred to as a ripple full-adder.

As illustrated, nth sum bit 595 is the product of an XOR operation at second XOR logic gate array 560b of the carryover bit 586 and the product of the first XOR logic gate array 560a of the nth input bit 512a and the nth input bit 512b. To produce the overflow bit 585, which is used as the carryover bit 586 for a subsequent full-adder circuit 505 in a ripple full-adder, the output of the first AND logic gate array 520a and the output of the second AND gate array 520b are ORed by OR logic gate array 530. The first AND logic gate array 520a uses the carryover bit 586 and the output of the first XOR logic gate array 560a as inputs, and the second AND logic gate array 520b uses the nth input bit 512a and the nth input bit 512b as inputs. For example, for the operation of one ($0001_{x2}$) plus three ($0011_{x2}$), the first sum bit 595 would be zero/FALSE (with an first overflow bit 585 of one/TRUE), the second sum bit 595 would be zero/FALSE (with an first overflow bit 585 of one/TRUE), the third sum bit 595 would be one/TRUE (with an first overflow bit 585 of zero/FALSE), to yield the sum of four ($0100_{x2}$) with zero/FALSE in the two least significant positions and one/TRUE in the second most significant position based on the order of output from the example bitwise full-adder circuit 505.

As will be understood, several rule circuits may be chained together, and the example rule circuits given herein are non-limiting examples of potential rules circuits that may be used to affect rules.

Figure 6:
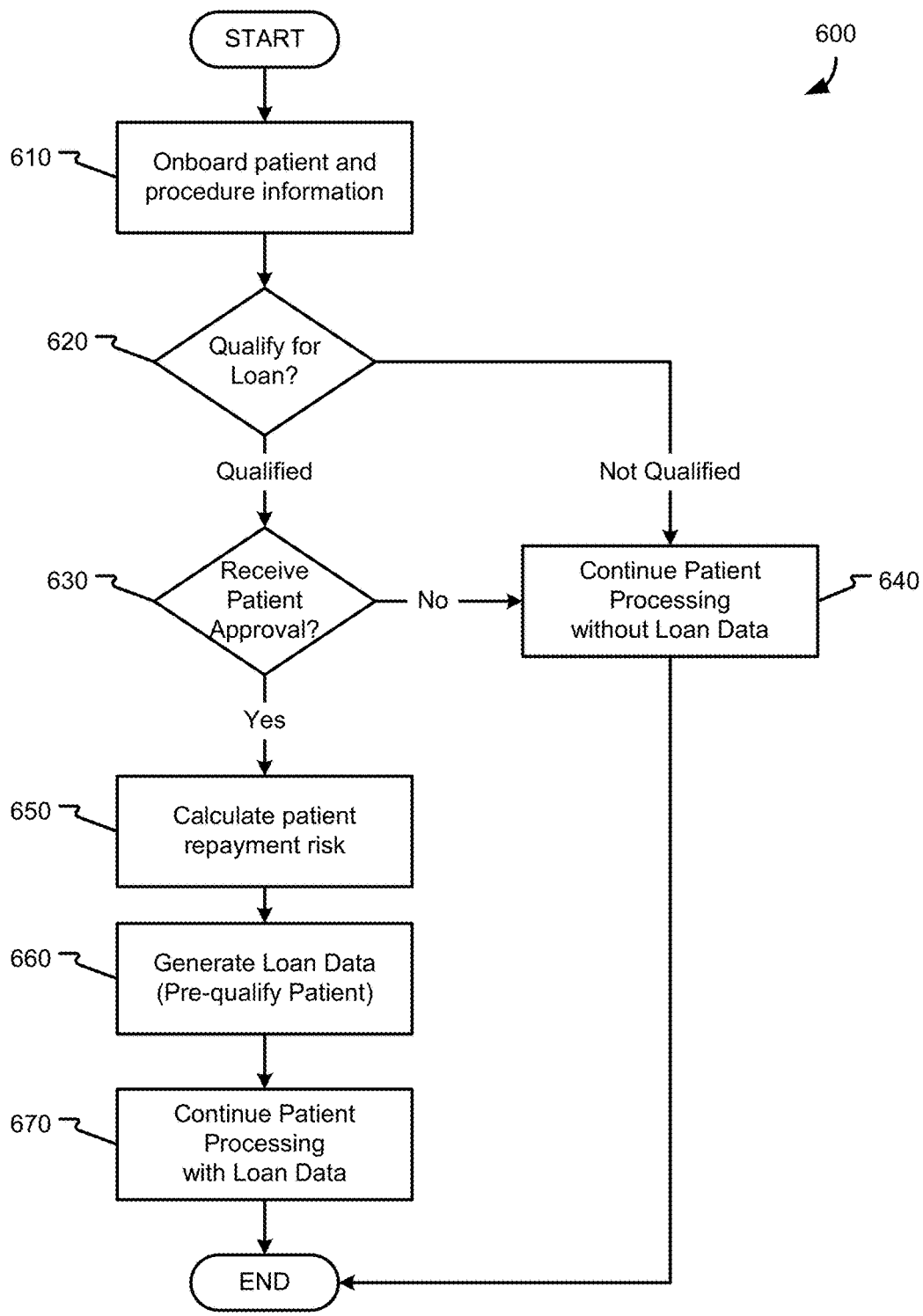
FIG. 6 is a flow chart showing general stages involved in an example method for improving the efficiency and capabilities of a patient access workflow system to integrate pre-procedure patient qualification.

FIG. 6 is a flow chart showing general stages involved in an example method 600 for improving the efficiency and capabilities of a PAWS 160 to integrate patient qualification. Method 600 begins at OPERATION 610, where patient and procedure information are onboarded to the PAWS 160, for example, by having those information input into a dashboard UI 180 or looked up from a database 150, based on information already entered into a dashboard UI 180. Such information includes, but is not limited to, patient data 132, insurance data 134, procedure data, healthcare provider repayment history data (e.g., aggregated historic payments data 138 for a given provider), and payment/charity policies for the healthcare provider.

At DECISION 620, it is determined whether the procedure qualifies for a loan for the patient. In various aspects, the decision is based on a cost of the procedure, a out-of-pocket cost to the patient (e.g., the cost of the procedure less insurance and any discounts), and whether charity or assistance will be provided to the patient. When it is determined that the procedure qualifies for one or more loans to be presented, method 600 proceeds to DECISION 630. When it is determined that the procedure does not qualify for one or more loans to be presented, method 600 proceeds to OPERATION 640.

At DECISION 630, it is determined whether the patient has given approval to the healthcare provider pre-qualify the patient for a loan. In various aspects, the approval may be given verbally, in writing, or via a biometric marker, and the approval (or rejection) may be stored electronically when it is given. When it is determined that the patient has given approval to pre-qualify for the loan, method 600 proceeds to OPERATION 650. When it is determined that the patient has not given approval to pre-qualify for the loan, method 600 proceeds to OPERATION 640.

At OPERATION 640, the patient continues to be processed via the PAWS 160 without generating loan data 140.

In various aspects, the continued processing may include a triage phase, a collection phase, a final overview phase, correction of errors or revisiting of previous phases where information was onboarded (to view or adjust inputted data), etc. Method 600 then concludes.

At OPERATION 650, a patient repayment risk is calculated. A risk assessment for the patient is calculated, based on the data that the system has been authorized to access. In various aspects, the decision analyzer 168, which may be part of the PAWs 160 or a separate service accessed by the PAWs 160, calculates the risk assessment based on information collected by the PAWs 160 during patient processing and from various databases 150 accessible by the decision analyzer 168. For example, the data onboarded during OPERATION 610 are used to lookup additional data about the patient from multiple sources. The multiple sources may provide previous payments data 138 associated with the patient with the healthcare provider or other healthcare providers, a credit score from a credit bureau, etc. These data may be compared against aggregated patient data 132 and payments data 138 for the healthcare provider, or aggregated from multiple healthcare providers in a specified field of medicine or region shared by the healthcare provider, to determine a risk assessment for the patient. The risk assessment provides a measure of the relative risk of the patient not paying for treatment compared to other patients (of the healthcare provider specifically, or similar providers generally).

Method 600 proceeds to OPERATION 660, where the risk assessment is used to generate the loan data 140 for the patient. In aspects, the loan data 140 are stored as tokens that include the terms of the loan, how the terms may be modified (e.g., in response to changing interest rates), how long the terms will be valid for (e.g., an expiration date), and the risk assessment of the patient. The tokenization of the loan data 140 is stored in a database 150 accessible by the PAWS 160 (or decision analyzer 168), which enables the PAWS 160 to provide the same terms to the patient at a later time without recalculation, and to transmit a single dataset to the selected lender when the patient chooses to apply for a loan presented by the PAWS 160 (either pre- or post-procedure, via the dashboard UI 180 or the portal UI 280, respectively). Alternatively, the lenders may have provided loan terms to the PAWS 160 in anticipation of loans or other assistance being offered to patients that are available to patients of the healthcare provider meeting given risk assessment and cost criteria, which are matched with the loan data 140 for the tokens. For example, these loans may be stored in a pool, from which the loan data 140 are generated, based on matching the risk assessment and procedure costs to the terms of the loan offers in the pool. Tokens are deleted from the database 150 when they are no longer valid (e.g., when a different token is selected by a patient, the token is not selected by an expiration date, another patient selects the loan associated with the token and no equivalent remains available).

At OPERATION 670, the patient continues to be processed via the PAWS 160 with the loan data 140. In various aspects, the continued processing may include a triage phase, a collection phase, a final overview phase, correction of errors or revisiting of previous phases where information was onboarded (to view or adjust inputted data), etc. In various aspects, the loan data 140 may be stored by the PAWS 160 as tokens for the patient to access at a later date via a portal UI 280. Method 600 then concludes.

Figure 7:
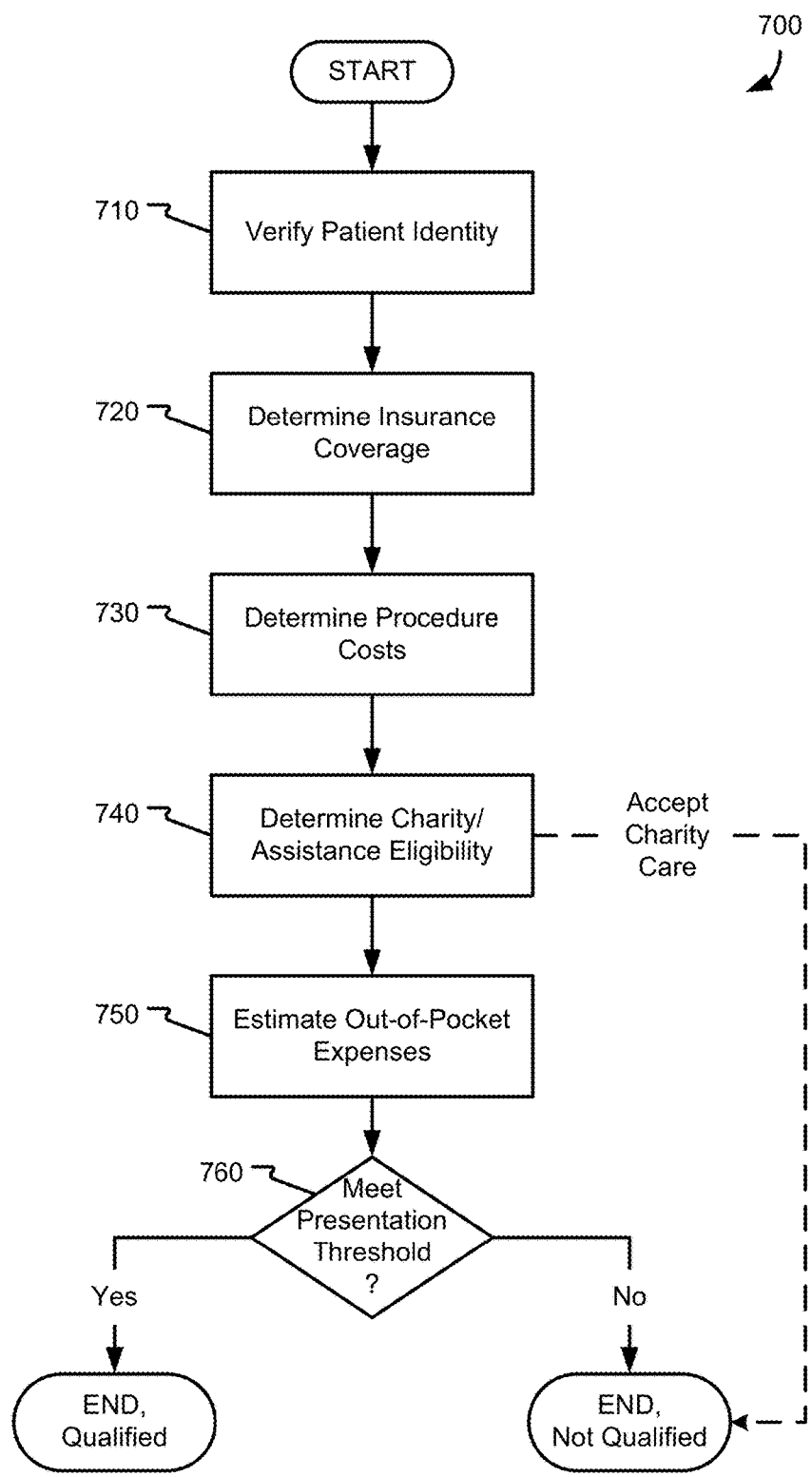
FIG. 7 is a flow chart showing general stages involved in an example method for determining whether a patient qualifies for a loan to be presented in an improved patient access workflow system.

FIG. 7 is a flow chart showing general stages involved in an example method 700 for determining whether a patient qualifies for a loan to be presented in an improved PAWS 160, for example, as part of DECISION 620 of method 600, discussed in regard to FIG. 6.

Method 700 begins at OPERATION 710, where the identity of the patient being processed is verified. In various aspects, the name, SSN, address, account number (including Medical Record Numbers (MRN)), a personal identification number (PIN), biometric marker, signature, other identifier, or combinations thereof are cross-correlated to verify the identity of the patient in multiple sources of information. For example, a database 150 may be queried for data on a patient having the name John Doe, but the database may provide records for all patients having the name John Doe, and the identifiers are used to select the records associated with the correct John Doe. Additionally or alternatively, the identifier may be used to verify that the data from the databases 150 are still valid. For example, a given patient may have moved to a new address, and therefore records that include an old address may be considered no longer applicable, and data from those records may be excluded from consideration.

Proceeding to OPERATION 720, the patient's insurance coverage is determined. In various aspects, the patient's insurance coverage is determined from the insurance data 134 entered when onboarding the patient for processing, or looked up from a database 150 in response to patient data 132 being onboarded for processing, if the patient has visited the healthcare provider before, or another healthcare provider who used the PAWS 160 that is authorized to share data with the healthcare provider. The insurance data 134 will identify an insurance provider (if any), any available secondary insurers (e.g., Medicare), and the particular plans to which the patient (or guarantor) is subscribed.

At OPERATION 730, the procedure costs are determined. In various aspects, this is accomplished by querying a database 150 for the costs associated with procedure, as set by the healthcare provider. In various aspects, the insurance coverage determined in OPERATION 720 will specify a contract for pricing between an insurance carrier and the healthcare provider, for example, specifying prices that the insurance carrier will accept for various diagnoses. In other aspects, the procedure costs are determined by the estimate analyzer 120, which uses transaction data 130 to determine the estimated costs of the procedures. When multiple procedures are part of a course of treatment, their associated costs may be added together for processing as one transaction, for example, by a full-adder circuit 505, or each procedure may be processed separately, for example, an ambulance ride and a subsequent emergency room visit may be billed separately or together.

The patient's eligibility for charity or assistance is determined at OPERATION 740. In various aspects, the patient's eligibility is only determined once the patient has provided authorization to check for eligibility. Patient data 132 are examined and compared to various assistance criteria, for example, via existence circuits 501, matching circuits 502, sizing circuits 504, or combinations thereof to determine if the patient data 132 indicate that the patient is available for charity care or assistance in procuring care. For example, the PAWS 160 may retrieve financial data relating to the patient that indicates a patient's earning status regarding the Federal Poverty Level, additional insurance programs that the patient is eligible for, demographic data for a charity's coverage area, etc. These criteria may be set by the healthcare provider (e.g., for a pro bono treatment program), by third party charities who provide criteria to the PAWS 160 (e.g., local, national, or international aid societies for various medical conditions), or governmental aid programs.

If at OPERATION 740, the patient is determined to qualify for charity care, and the charity is accepted, method 700 will conclude with a determination that the patient does not qualify for one or more loans to be presented. For example, if a third-party charity will pay for the patient's procedure, or the healthcare provider offers the procedure pro bono, the patient will not have expenses for the procedure, and therefore will not need a loan to help cover those expenses. This determination improves the operation and efficiency of the PAWS 160 by eliminated processing steps that are superfluous to process a given patient, thus conserving memory and processing resources.

At OPERATION 750 the out-of-pocket expenses for the procedure are calculated for the patient. In various aspects, the calculation is achieved via a series of subtractor circuits 503, that are part of the PAWS 160, which uses the cost of procedures determined in OPERATION 730 as the minuend, and any insurance offsets or assistance, determined in OPERATIONS 720 and 740, as the subtrahends.

Method 700 proceeds to DECISION 760, where it is determined whether a presentation threshold is met for the procedure to qualify for presenting loans. Thresholds may be based on a fixed cost (e.g., any procedure costing more than $X), a patient-specific financial analysis (e.g., any procedure costing more than Y % of a patient's yearly income), the duration of a procedure (e.g., any procedure taking more than Z visits to complete, such as, for example, a chemotherapy regimen, a series of corrective surgeries, prolonged observation, etc.), and combinations thereof.

For example, the out-of-pocket expense to a first patient for a given procedure may be $50, which falls below a fixed cost threshold to present loan offers to the patient. In a contrary example, the out-of-pocket expense to a second patient for the same procedure at the same healthcare provider may be $5,000 (due to differences in insurance, etc.), which exceeds a threshold to present loan offers to the patient. In another example, when a patient (who would not ordinarily qualify for a loan based on a fixed cost threshold) authorizes the access to patient-specific financial data, the patient may qualify for loan presentation based on a financial analysis threshold, stating that the cost of the procedure exceeds a given percent of the patient's income. Similarly, when a patient does not qualify for a loan based on a financial analysis threshold (or a fixed cost threshold), but the procedure will take an extended period of time (including recuperation), the loans may be presented if a duration threshold is exceeded, which may be used to alter any fixed cost thresholds or financial analysis thresholds or as a stand-alone threshold, to account for time away from work involved with the procedure, which may affect the need for a loan.

When it is determined that the presentation threshold has been met at DECISION 760, method 700 concludes with a determination that the patient qualifies for one or more loans to be presented. When it is determined that the presentation threshold has not been met at DECISION 760, method 700 concludes with a determination that the patient does not qualify for one or more loans to be presented.

Figure 8:
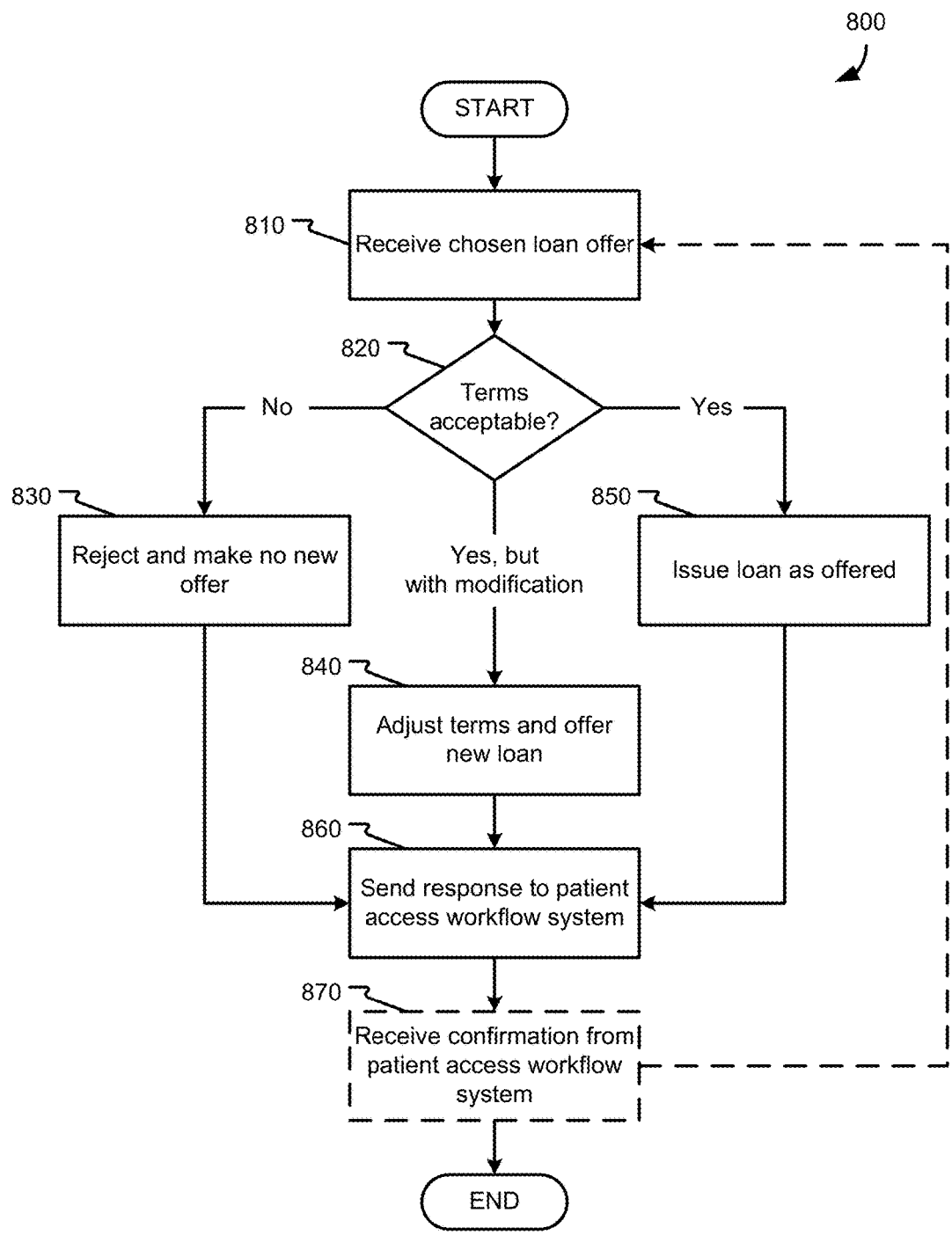
FIG. 8 is a flow chart showing general stages involved in an example method for confirming a chosen loan offer with reduced bandwidth usage.

FIG. 8 is a flow chart showing general stages involved in an example method 800 for confirming a chosen loan offer with reduced bandwidth usage. Method 800 begins at OPERATION 810 when a lender associated with a chosen loan offer (e.g., an offer selected by the patient) receives the corresponding loan offer from the PAWS 160. In various aspects, the chosen loan may have been selected pre-procedure, for example via the dashboard UI 180, or post-procedure, for example via the portal UI 280. The chosen loan offer may be transmitted as a token, including the original loan data 140 for the offer (including the offered terms—principal, interest rate, length, etc.), the patient risk assessment determined by the PAWS 160, an expiration date for the offers, and/or modification data including ranges by which the lender or the PAWS 160 may modify offered terms for re-presentation to the patient.

Method 800 proceeds to DECISION 820, where the lender determines whether the terms are acceptable to it. At DECISION 820 the lender may decide that: the terms of the chosen loan offer are not acceptable, and method 800 will proceed to OPERATION 830; that the terms of the chose loan offer are not acceptable, but are modifiable to be acceptable within an acceptable range, and method 800 will proceed to OPERATION 840; or the chosen loan offer is acceptable, and method 800 will proceed to OPERATION 850.

In aspects where the PAWS 160 estimated the terms of a loan that the lender would offer to the patient to cover the costs of a procedure, (e.g., so that multiple loan offers can be presented to the patient during an estimation phase of pre-procedure processing of the patient without communicating with multiple potential lenders regarding the given patient or procedure), the lender may decide that the terms it received in OPERATION 810 are acceptable or unacceptable for a given patient and procedure. In other aspects, where the PAWS 160 selected a loan from a pool of pre-supplied loans from the lender (supplied as either just-in-time quotes or several lines of credit given to the healthcare provider that may be re-assigned to patients meeting certain criteria), the lender may decide whether the pre-supplied loan is still valid (e.g., not expired) or is valid with a modification from what was presented to the patient (e.g., a basis interest rate has been adjusted, an initial or recurring billing date will be moved, parties will be substituted).

At OPERATION 830 the lender rejects the chosen loan offer received in OPERATION 810, and no new offer is made. Method 800 then proceeds to OPERATION 860, where a response is transmitted to the PAWS 160 indicating that the lender has declined to offer terms for a loan as chosen by the patient. Method 800 optionally proceeds to OPTIONAL OPERATION 870, where a confirmation is received from the PAWS 160, acknowledging the rejection, and potentially including a new chosen loan offer for the lender, in which case method 800 returns to OPERATION 810. Otherwise, method 800 concludes.

At OPERATION 840 the lender adjusts the terms of the chosen loan offer received in OPERATION 810 and makes a new offer with the adjusted terms. In various aspects, the chosen loan offer received in OPERATION 810 includes modification data, and the lender adjusts the chosen loan within the ranges specified by the modification data. For example, the chosen loan offer may be for a loan for X dollars, with n % interest, payable over Y years and includes modification data allowing the interest rate to be accepted by the lender if it varies no more than m (i.e., between (n-m) and (n+m)). Alternatively, the patient may have been offered a loan with terms that allow the lender flexibility in choosing a term. For example, the offered loan may be for X dollars, with an interest rate between n % and m %, payable over Y years. In yet other aspects, the terms selected by the patient from the dashboard UI 180 are locked in, and if the lender adjusts the terms, the patient will still be provided the originally-offered terms and the healthcare service provider will be responsible for a difference in the adjusted terms.

After the chosen loan offer's terms are adjusted, a new loan is offered and a response is transmitted to the PAWS 160 in OPERATION 860 that includes the new loan offer. Method 800 optionally proceeds to OPTIONAL OPERATION 870, where a confirmation is received from the PAWS 160, acknowledging the new loan offer, and potentially selecting the new loan offer as the chosen loan offer, in which case method 800 returns to OPERATION 810. Otherwise, such as when no confirmation is received or the patient rejects the new loan offer in the confirmation, method 800 concludes.

At OPERATION 850 the lender issues the loan as offered. Method 800 then proceeds to OPERATION 860 where the issuance of the loan as offered is transmitted to the PAWS 160 in a response. Method 800 then proceeds to OPTIONAL OPERATION 870 where a confirmation from the PAWS 160 is received, which, in various aspects includes account information from the healthcare provider system 220 to transfer the account and patient data 132 to the banking system 210 to service the accepted loan. Method 800 then concludes.

Figure 9:
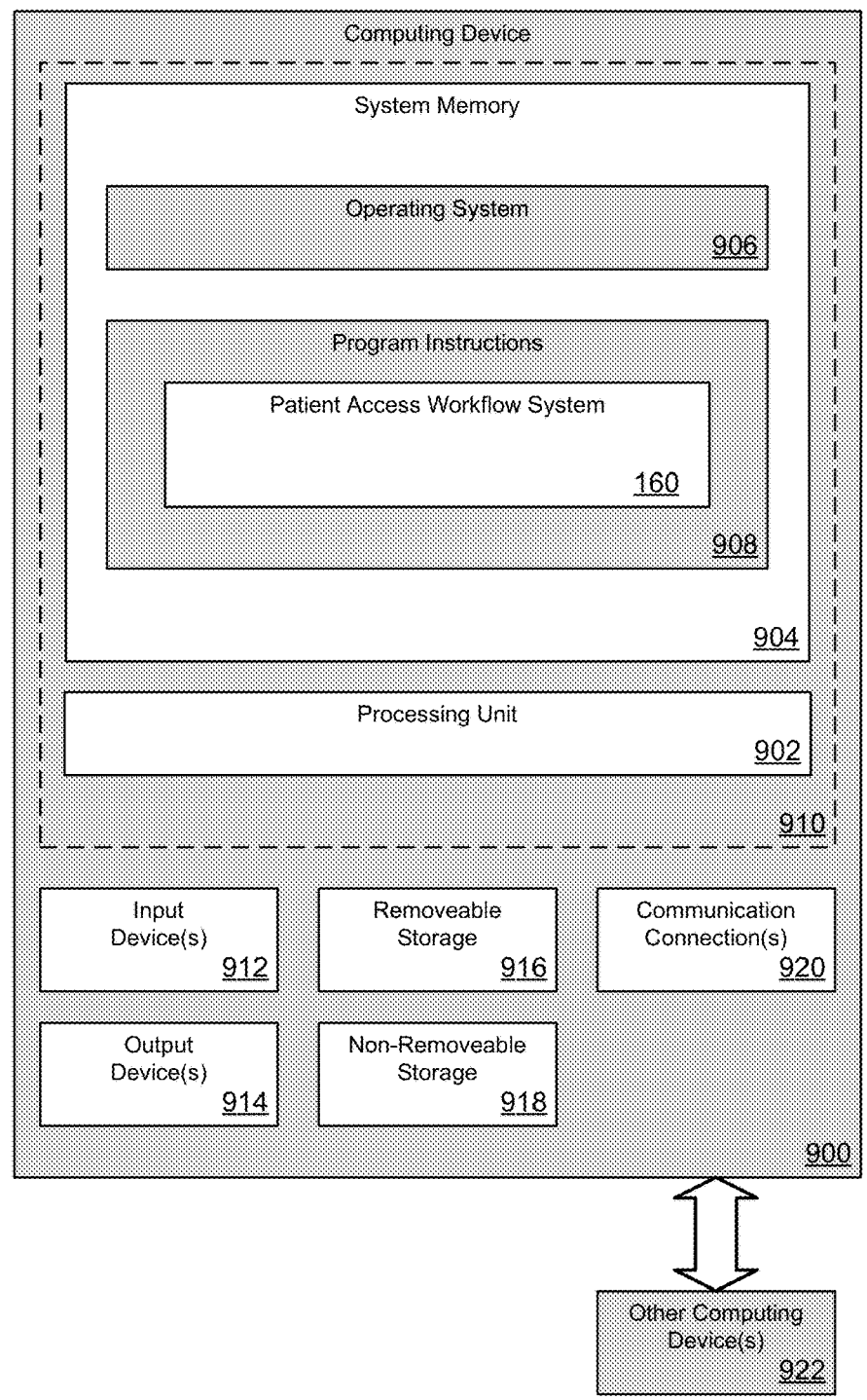
FIG. 9 is a block diagram illustrating physical components of an example computing device with which aspects may be practiced.

FIG. 9 is a block diagram illustrating physical components of an example computing device with which aspects may be practiced. The computing device 900 may include at least one processing unit 902 and a system memory 904. The system memory 904 may comprise, but is not limited to, volatile (e.g. random access memory (RAM)), non-volatile (e.g. read-only memory (ROM)), flash memory, or any combination thereof. System memory 904 may include operating system 906, one or more program instructions 908, and may include sufficient computer-executable instructions for a patient access workflow system 160, which when executed, perform functionalities as described herein. Operating system 906, for example, may be suitable for controlling the operation of computing device 900. Furthermore, aspects may be practiced in conjunction with a graphics library, other operating systems, or any other application program and is not limited to any particular application or system. This basic configuration is illustrated by those components within a dashed line 910. Computing device 900 may also include one or more input device(s) 912 (keyboard, mouse, pen, touch input device, etc.) and one or more output device(s) 914 (e.g., display, speakers, a printer, etc.).

The computing device 900 may also include additional data storage devices (removable or non-removable) such as, for example, magnetic disks, optical disks, or tape. Such additional storage is illustrated by a removable storage 916 and a non-removable storage 918. Computing device 900 may also contain a communication connection 920 that may allow computing device 900 to communicate with other computing devices 922, such as over a network in a distributed computing environment, for example, an intranet or the Internet. Communication connection 920 is one example of a communication medium, via which computer-readable transmission media (i.e., signals) may be propagated.

Programming modules may include routines, programs, components, data structures, and other types of structures that may perform particular tasks or that may implement particular abstract data types. Moreover, aspects may be practiced with other computer system configurations, including hand-held devices, multiprocessor systems, microprocessor-based or programmable user electronics, minicomputers, mainframe computers, and the like. Aspects may also be practiced in distributed computing environments where tasks are performed by remote processing devices that are linked through a communications network. In a distributed computing environment, programming modules may be located in both local and remote memory storage devices.

Furthermore, aspects may be practiced in an electrical circuit comprising discrete electronic elements, packaged or integrated electronic chips containing logic gates, a circuit using a microprocessor, or on a single chip containing electronic elements or microprocessors (e.g., a system-on-a-chip (SoC)). Aspects may also be practiced using other technologies capable of performing logical operations such as, for example, AND, OR, and NOT, including, but not limited to, mechanical, optical, fluidic, and quantum technologies. In addition, aspects may be practiced within a general purpose computer or in any other circuits or systems.

Aspects may be implemented as a computer process (method), a computing system, or as an article of manufacture, such as a computer program product or computer-readable storage medium. The computer program product may be a computer storage medium readable by a computer system and encoding a computer program of instructions for executing a computer process. Accordingly, hardware or software (including firmware, resident software, microcode, etc.) may provide aspects discussed herein. Aspects may take the form of a computer program product on a computer-usable or computer-readable storage medium having computer-usable or computer-readable program code embodied in the medium for use by, or in connection with, an instruction execution system.

Although aspects have been described as being associated with data stored in memory and other storage mediums, data can also be stored on or read from other types of computer-readable media, such as secondary storage devices, like hard disks, floppy disks, or a CD-ROM, or other forms of RAM or ROM. The term computer-readable storage medium refers only to devices and articles of manufacture that store data or computer-executable instructions readable by a computing device. The term computer-readable storage media do not include computer-readable transmission media.

Aspects of the present invention may be used in various distributed computing environments where tasks are performed by remote processing devices that are linked through a communications network.

Aspects of the invention may be implemented via local and remote computing and data storage systems. Such memory storage and processing units may be implemented in a computing device. Any suitable combination of hardware, software, or firmware may be used to implement the memory storage and processing unit. For example, the memory storage and processing unit may be implemented with computing device 900 or any other computing devices 922, in combination with computing device 900, wherein functionality may be brought together over a network in a distributed computing environment, for example, an intranet or the Internet, to perform the functions as described herein. The systems, devices, and processors described herein are provided as examples; however, other systems, devices, and processors may comprise the aforementioned memory storage and processing unit, consistent with the described aspects.

The description and illustration of one or more aspects provided in this application are intended to provide a thorough and complete disclosure the full scope of the subject matter to those skilled in the art and are not intended to limit or restrict the scope of the invention as claimed in any way. The aspects, examples, and details provided in this application are considered sufficient to convey possession and enable those skilled in the art to practice the best mode of the claimed invention. Descriptions of structures, resources, operations, and acts considered well-known to those skilled in the art may be brief or omitted to avoid obscuring lesser known or unique aspects of the subject matter of this application. The claimed invention should not be construed as being limited to any embodiment, aspects, example, or detail provided in this application unless expressly stated herein. Regardless of whether shown or described collectively or separately, the various features (both structural and methodological) are intended to be selectively included or omitted to produce an embodiment with a particular set of features. Further, any or all of the functions and acts shown or described may be performed in any order or concurrently. Having been provided with the description and illustration of the present application, one skilled in the art may envision variations, modifications, and alternate embodiments falling within the spirit of the broader aspects of the general inventive concept provided in this application that do not depart from the broader scope of the present disclosure.

We claim:

1. A circuit for improving efficiency of a services access workflow system, comprising:
    a first aggregating OR logic gate array;
    a second aggregating OR logic gate array; and
    a plurality of bitwise sizing circuits, wherein each bitwise sizing circuit of the plurality of sizing circuits comprise:
        a first input, receiving a first data source bit from a first data source;
        a second input, receiving a second data source bit from a second data source;
        an inverter, receiving an overrun bit to produce an inverted overrun bit;
        a XOR logic gate array, accepting the first data source bit and the second data source bit to produce a XOR product;
        a first AND logic gate array, accepting the first data source bit, the inverted overrun bit, and the XOR product to produce a first exceed bit;
        a second AND logic gate array, accepting the second data source bit, the inverted overrun bit, and the XOR product to produce a second exceed bit; and
        an OR logic gate array, accepting the first exceed bit and the second exceed bit to produce a variance bit;
    wherein the plurality of bitwise sizing circuits are organized in series as a chain, such that each of the bitwise sizing circuits of the chain, subsequent to a first bitwise sizing circuit in the chain, are communicated to an immediately previous bitwise sizing circuit in the chain such that the variance bit of the immediately previous bitwise sizing circuit is received by the inverter of the bitwise sizing circuit as the overrun bit;
    wherein the first data source includes an input value;
    wherein the second data source includes a threshold value;
    wherein the chain receives data starting with most significant bits of the input value and the threshold value;
    wherein the first exceed bit from each of the plurality of bitwise sizing circuits are combined via the first aggregating OR logic gate array to produce a first aggregated exceed bit;
    wherein the second exceed bit from each of the plurality of bitwise sizing circuits are combined via the second aggregating OR logic gate array to produce a second aggregated exceed bit;
    wherein the services access workflow system uses the first aggregated exceed bit and the second aggregated exceed bit to determine that loan data qualifies for presentation via the services access workflow system when the first aggregated exceed bit is one/TRUE.

2. The circuit of claim 1, wherein the threshold value is for a charity care program income requirement, and wherein the input value is an annual income of a person to whom the loan data is intended to be presented via the services access workflow system.

3. The circuit of claim 2, wherein the services access workflow system uses the first aggregated exceed bit to determine to generate the loan data when the first aggregated exceed bit is one/TRUE.

4. The circuit of claim 1, wherein the threshold value is for a cost threshold, and wherein the input value is an out-of-pocket expense to a person to whom the loan data is intended to be presented via the services access workflow system.

5. The circuit of claim 4, wherein the out-of-pocket expense is calculated by the service access workflow system by subtracting an insurance offset from an initial cost of a service.

6. The circuit of claim 4, wherein the services access workflow system alters the cost threshold using:
    a fixed cost of the service;
    an annual income of a person to whom the loan data is intended to be presented via the services access workflow system; and
    a period of time in which the service will be rendered.

7. The circuit of claim 1, wherein the threshold value includes a preference of a number of selection controls to display in a graphical user interface of the service access workflow system, and the input value includes a number of offers returned in the loan data;
    wherein each selection control is associated with one offer of the loan data and is selectable via the graphical user interface to initiate communication between the services access workflow system and a lender associated with the one offer; and
    wherein the services access workflow system uses the first aggregated exceed bit and the second aggregated exceed bit to determine that all of the selection controls are to be presented via the graphical user interface of the services access workflow system when the second aggregated exceed bit is zero/FALSE, and that a subset of the selection controls are to be presented via the graphical user interface of the services access workflow system when the second aggregated exceed bit is one/TRUE.

8. The circuit of claim 1, wherein when the input value comprises fewer bits than the threshold value, the input value is padded with significant bits set to zero/FALSE until the input value comprises an equal number of bits to the threshold value.

9. The circuit of claim 1, wherein logic gate arrays comprising the circuit include transistors provided by a processor of the service access workflow system.

10. The circuit of claim 1, wherein the first data source stores the input value as characters encodings of a number, and wherein the service access workflow system converts the character encodings to a binary form of the number before the input value is provided to the circuit.

* * * * *